US007729559B2

(12) United States Patent
ÓRuanaidh et al.

(10) Patent No.: US 7,729,559 B2
(45) Date of Patent: Jun. 1, 2010

(54) SYSTEM AND METHOD FOR OPTICAL SECTION IMAGE LINE REMOVAL

(75) Inventors: Joseph John Kevin Ó Ruanaidh, Hamilton, NJ (US); Yang Zhang, Bridgewater, NJ (US); Pierre Emeric, Princeton, NJ (US); Marcin R. Swiatek, Branchburg, NJ (US); Vadim Rozenfeld, Piscataway, NJ (US)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 985 days.

(21) Appl. No.: 11/419,566

(22) Filed: May 22, 2006

(65) Prior Publication Data

US 2007/0269134 A1 Nov. 22, 2007

(51) Int. Cl.
*G06K 9/40* (2006.01)
(52) U.S. Cl. ...................................................... 382/275
(58) Field of Classification Search .................. 382/275
See application file for complete search history.

(56) References Cited

U.S. PATENT DOCUMENTS

| | | | | |
|---|---|---|---|---|
| 4,742,544 A | * | 5/1988 | Kupnicki et al. | 380/215 |
| 5,218,299 A | * | 6/1993 | Dunkel | 324/307 |
| 5,715,334 A | * | 2/1998 | Peters | 382/254 |
| 5,818,957 A | * | 10/1998 | Mammone | 382/128 |
| 5,937,103 A | * | 8/1999 | Oh et al. | 382/276 |
| 6,282,326 B1 | * | 8/2001 | Lee et al. | 382/289 |
| 6,584,233 B1 | * | 6/2003 | Kane et al. | 382/254 |
| 2001/0033638 A1 | * | 10/2001 | Inoue | 378/154 |
| 2002/0085217 A1 | * | 7/2002 | Sakaue et al. | 358/1.9 |
| 2002/0196901 A1 | * | 12/2002 | Inoue | 378/154 |
| 2003/0133608 A1 | * | 7/2003 | Bernstein et al. | 382/163 |
| 2005/0057756 A1 | * | 3/2005 | Fang-Yen et al. | 356/497 |
| 2005/0200704 A1 | * | 9/2005 | Kodake et al. | 348/207.99 |
| 2007/0177820 A1 | * | 8/2007 | O Ruanaidh et al. | 382/294 |

FOREIGN PATENT DOCUMENTS

JP 2000023040 A * 1/2000

OTHER PUBLICATIONS

Machine translation of JP 2000023040 A, Morohoshi et al.*
Neil, M., et al., "Method of Obtaining Optical Sectioning by Using Structured Light in a Conventional Microscope". Optics Letters (1997) vol. 22, No. 24, pp. 1805-1807.
Schaefer, L., et al., "Structured illumination microscopy: artefact analysis and reduction utilizing a parameter optimization approach". Journal of Microscopy (2004) vol. 216, No. 2, pp. 165-174.

* cited by examiner

*Primary Examiner*—Bhavesh M Mehta
*Assistant Examiner*—David P Rashid
(74) *Attorney, Agent, or Firm*—Yonggang Ji

(57) ABSTRACT

An apparatus, system, and method for generating an image are disclosed. A processor may generate a first output image based on a plurality of input images and remove an artefact, if any, from the first output image to generate a second output image. For example, in an embodiment, the processor may calculate a contribution of the artefact to image intensity values and subtract the calculated contribution from the image intensity values. In another embodiment, the processor may delete a predetermined portion of a transform image representing transform data obtained by applying an image transform to the first output image, thereby modifying the transform data, and may generate a non-transform image based on the modified transform data.

40 Claims, 16 Drawing Sheets

SYSTEM AND METHOD FOR OPTICAL SECTION IMAGE LINE REMOVAL

FIELD OF THE INVENTION

This invention relates to a system for removing a line from a section of an optical image.

BACKGROUND OF THE INVENTION

Obtaining a two dimensional image of a three dimensional object is often desired, for example, for the study of organisms. Imaging of the object is often conducted via a microscope. Clarity of the image is enhanced by imaging a particular two dimensional plane, a slice, of the three dimensional object.

Conventional systems generate an image of the two dimensional plane in the three dimensional object in several different ways, including deconvolution, confocal laser scanning, and optical sectioning. For optical sectioning, conventional systems project a grid pattern onto a particular plane in the three dimensional image, and construct an image out of only those pixels in which the grid pattern falls. The plane is one selected with respect to an objective. The plane of the object to be imaged depends on the object's placement with respect to the selected plane. The grid pattern refers to a pattern of changing light intensities which can be graphed as a sine wave measured in terms of pixels, so that the peak and lowest intensities occur cyclically every given number of pixels. FIG. 1 is a diagram that illustrates components of a conventional system for performing optical sectioning, for example, a microscope. A lamp 100 emits light that is radiated onto a grid 102 of horizontal lines and that is subsequently reflected by a beam splitter 104 as the grid pattern onto the object to be imaged. Light reflected by the object, including the grid pattern, is then captured as an image by a camera 106. The image is processed by a processor 108 to generate an output image. In particular, the processor 108 provides an output image constructed of only those pixels in which the grid pattern falls.

While projecting the grid pattern onto the object allows for removal of those pixels that are not of the desired plane of the object, it also adds to the obtained image an unwanted grid pattern. Accordingly, the grid 102 is moved to multiple positions, an image is obtained at each of the positions, and the images are combined to form a single image without grid lines. A piezo-electrically driven actuator 110 is provided to move the grid 102. The piezo-electrically driven actuator 110 responds to input voltages. The voltages may be generated, for example, by the processor 108. The extent to which the piezo-electrically driven actuator 110 moves the grid 102 depends on the particular voltages applied to the piezo-electrically driven actuator 110. The particular parts of the object on which particular intensities of the grid pattern are projected depend on the position of the grid 102. The piezo-electrically driven actuator 110 is moved to move the grid between three positions. The positions are set so that the resultant intensities of corresponding grid patterns can be graphed as corresponding sine waves, where a particular point in the sine wave is phase shifted between the three grid patterns by equal phase angles, i.e., phase angles of 0 degrees, 120 degrees, and 240 degrees, each separated by 120 degrees. For each of the three positions of the grid 102, the camera 106 captures a corresponding image. FIG. 2 shows the 3 images superimposed onto each other and their corresponding grid line intensity graphs.

For each pixel, the processor 108 combines the values obtained from each of the three images using the formula $I_P = \alpha \sqrt{(I_1-I_2)^2 + (I_2-I_3)^2 + (I_3-I_1)^2}$, where $I_P$ represents the combined pixel value, $I_1$, $I_2$, and $I_3$ each represents a pixel value for a respective one of the three images, and $\alpha$ equals $$\frac{\sqrt{2}}{3}.$$

Since the grid pattern is phased by equal amounts of 120°, i.e., the phase angles are 0°, 120°, and 240°, the sine waves of the grid pattern at a particular pixel in the three images cancel each other out, i.e., their values average to zero. Further, a widefield image, i.e., the portion of the images at which the grid patterns are not in focus, are canceled out by $I_1-I_2$, $I_2-I_3$, and $I_3-I_1$. Accordingly, the value of $I_P$ determined by the combination of the three images does not include the value of the corresponding point in the grid line. The output image therefore does not include the grid lines.

In order to ensure that voltages applied to the piezo-electrically driven actuator 110 are such that cause the piezo-electrically driven actuator 110 to move the grid 102 by the correct amount, where the grid pattern is phase shifted by 120 degrees, some or all conventional systems require calibration. For calibration, an object having a substantially uniform surface, such as a smooth mirror, is inserted as the object to be imaged, and three images are captured as discussed above. If the phases are incorrect, an artefact, which is a harmonic of the grid pattern frequency, appears in the combined image. Accordingly, the voltages applied to the piezo-electrically driven actuator 110, and therefore the phases, are repeatedly changed. For each change, three images are recorded and the signal power of the artefact in the combined image is measured using a Fast Fourier Transform (FFT). The changes are repeated until the signal power is determined to be below a certain threshold, indicating substantial removal of the artefact, which corresponds to approximately correct phase shifts. Once the approximately correct phase shifts are obtained, the calibration is complete.

This procedure requires combining the pixel values of each set of three images for analysis of the artefact. The procedure typically takes 45 seconds, but can take as long as 5 minutes. Further, the phase angles are not directly determined. Instead, that which approximately corresponds to an instance where the images are at the desired phase angles, i.e., a reduction below a threshold of an artefact signal, is obtained. This procedure does not allow for accurately obtaining the desired phase angles. Further, the instance where the artefact signal is below the threshold cannot be accurately determined using FFT, in particular considering the low accuracy of FFT, which can be attributed at least in part to the measurement of the signal power in discrete values. Therefore, grid lines and/or an artefact are not completely removed from the image.

Additionally, the pixel values returned by the camera 106 are often imprecise with respect to values of image intensity. Accordingly, the measurement of the intensity of the artefact is often incorrect. The piezo-electrically driven actuator 110 is therefore incorrectly calibrated.

Furthermore, regardless of the preciseness of the calibration procedure, the output image obtained by combining the three images often includes an artefact. The artefact is often a sinusoidal variance in image intensity similar to the grid pattern. Though the sinusoidal variance of the artefact is not necessarily at a same frequency as that of the grid pattern, it is usually a product of the grid pattern and is at some harmonic of the grid pattern's sine wave. There are a number of possible causes for the artefact. An example cause is a misalignment of parts, such as the piezo-electrically driven actuator 110, which causes a change in intensities of pixel values between images (other than the intensity variance caused by the grid pattern itself). Such change in intensities results in a non-cancellation of the grid pattern of the three images when combined. Other factors may also contribute to an artefact.

Additionally, while the combination of the three images allows for the removal of grid lines, the procedure does not yield an optimal image.

Accordingly, there is a need in the art for a system and method that efficiently calibrates movement of the grid 102, and provides an optimal image without grid lines or an artefact.

SUMMARY OF THE INVENTION

Embodiments of the present invention relate to an apparatus, computer system, and method for generating an image via optical sectioning by determining phase angles of a grid pattern projected successively onto an object to be imaged. Embodiments of the present invention relate to an apparatus, computer system, and method for generating an image based on phase angles of a grid pattern that are set or determined with reference to pixel values that are logarithmic values or approximate logarithmic pixel values of actually recorded pixel values. Embodiments of the present invention relate to an apparatus, computer system, and method for generating an image based on values of a plurality of images that includes more than three images combined, in particular where images of each pair of successive ones of the plurality of images is obtained at a different phase angle, i.e., no image is at a same phase angle as that of its immediately preceding image. Successive images, as used herein, refers to succession with regard to grid pattern phase angles, rather than succession in time of recordation. Embodiments of the present invention relate to an apparatus, computer system, and method for removing an artefact from an output image generated via optical sectioning.

The computer system may include a computer program written in any conventional computer language. Example computer languages that may be used to implement the computer system and method of the present invention may be C and/or MATLAB® numerical computing environment.

DETAILED DESCRIPTION OF THE INVENTION

Direct Calculation of Phase Angle

Figure 1:
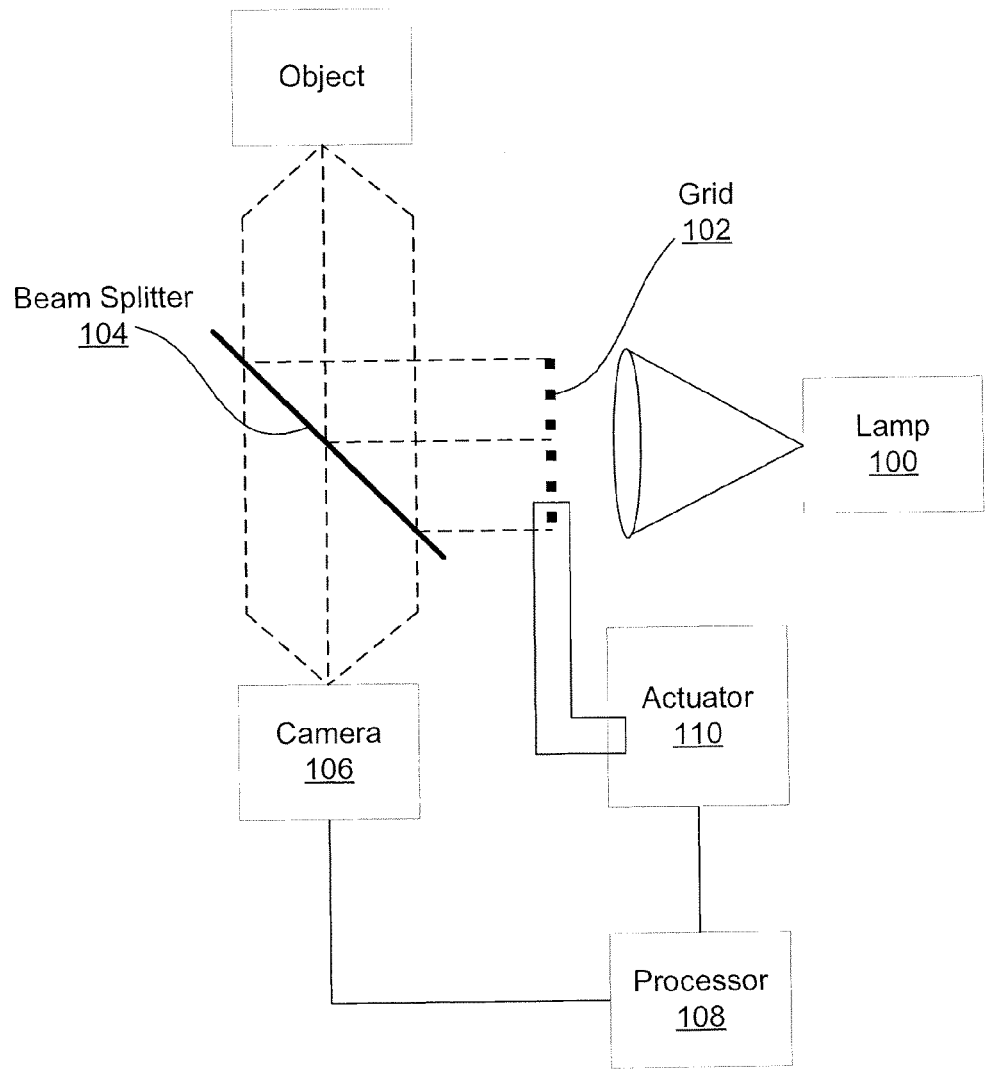
FIG. 1 is a block diagram that illustrates components of a conventional imaging system for performing optical sectioning.
Figure 2:
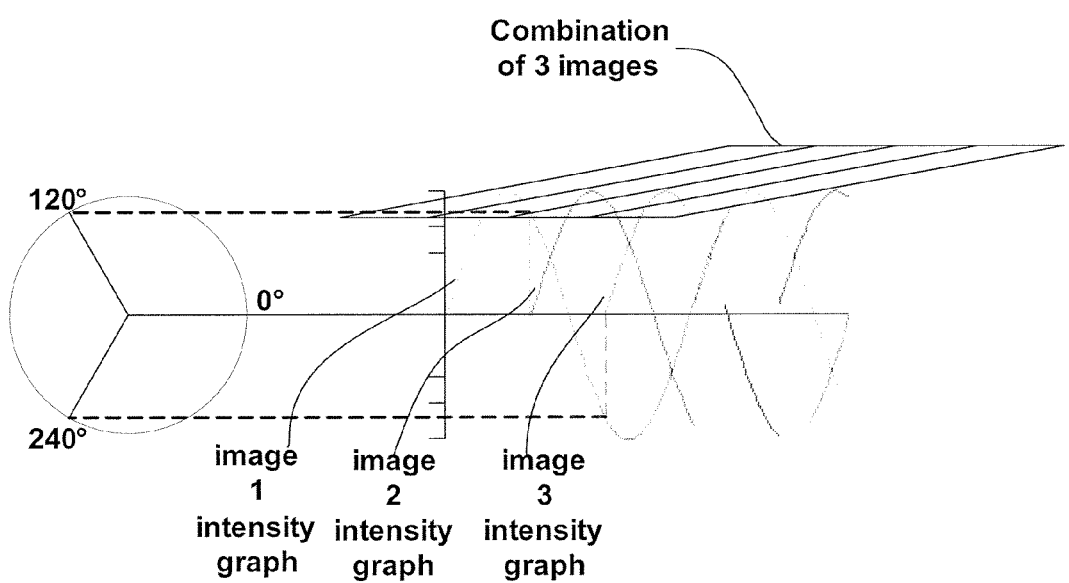
FIG. 2 illustrates a superimposition of three images recorded in a conventional system and their respective grid pattern intensities.
Figure 3:
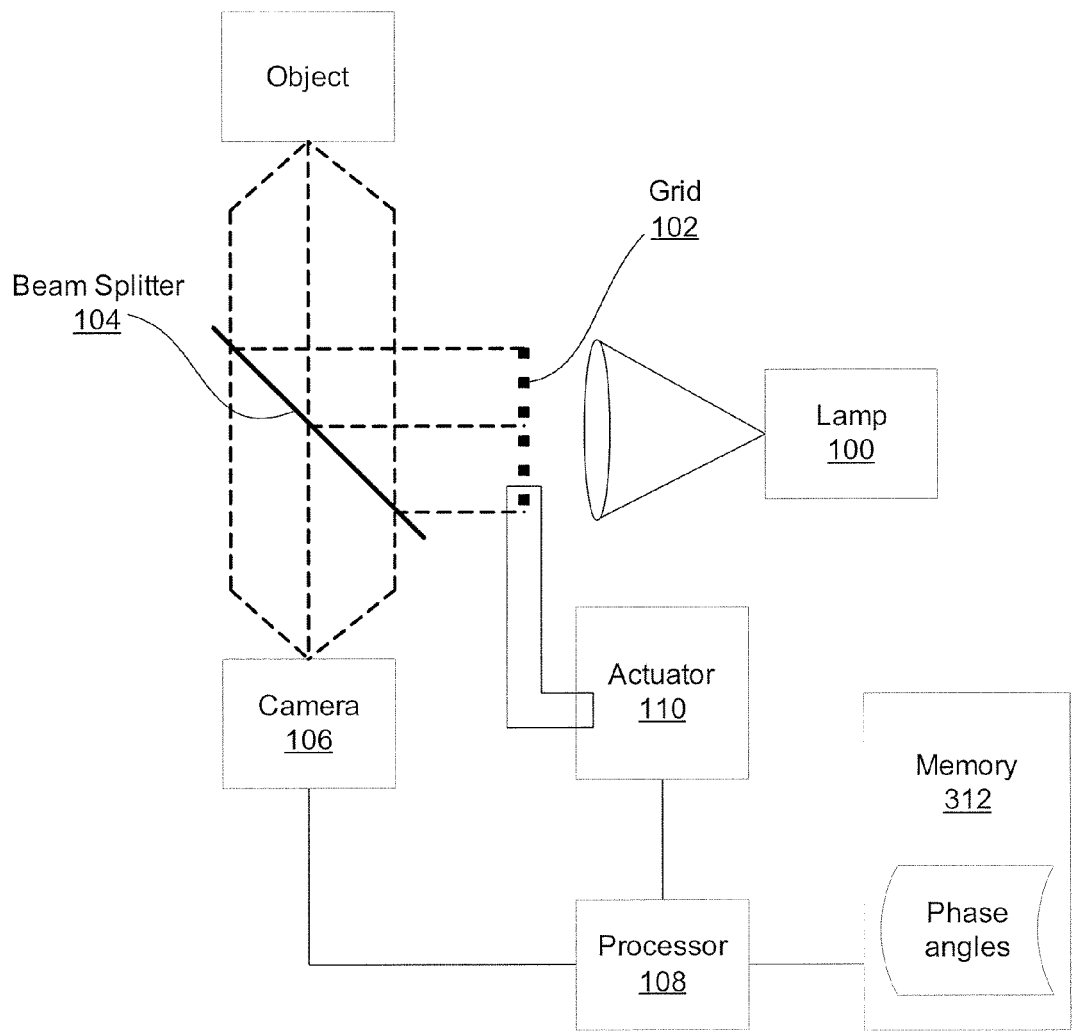
FIG. 3 is a block diagram that illustrates example components of an imaging system according to an example embodiment of the present invention.

FIG. 3 illustrates components of an imaging system according to an embodiment of the present invention. Elements of FIG. 3 which are described above with respect to FIG. 1 are provided with the same reference numerals. Referring to FIG. 3, in an embodiment of the present invention, for obtaining an image of an object, the grid 102 may be moved by the piezo-electrically driven actuator 110 into three different positions. It will be appreciated that an actuator other than a piezo-electrically driven actuator may be used. Each position may be at a different phase angle. For each of the three positions, the camera 106, e.g., a CCD (charge-coupled device) camera or other conventional camera, may record a corresponding image including grid lines. The processor 108, which may be any suitably appropriate computer processor or equivalent thereof, may generate an output image based on the three recorded images. The processor 108 may be of any suitably appropriate computing device, e.g., a computer, personal digital assistant (PDA), laptop computer, notebook computer, mobile telephone, a hard-drive based device, or any device that can receive, send, and store data.

Three grid positions and corresponding images may be used in order to generate an output image based on images corresponding to grid phase angles that are offset by 120°. Alternatively, three grid positions and corresponding images, even if not offset by 120°, may be used in order to provide for each pixel three equations, one equation per image. Each equation may include three unknown variables that correspond to components of the pixel value. Each equation may be $I_n = I_w + I_c \cos \phi_n + I_s \sin \phi_n$, where $I_n$ represents a pixel value of a particular image n of the three images, $I_w$ represents the widefield component of the pixel value, $\phi_n$ represents the phase angle of the particular image n, $I_c$ represents the in-phase component, and $I_s$ represents the quadrature component. If the respective phase angles of the three images are determined, the values of the unknowns $I_w$, $I_c$, and $I_s$ may be calculated since three equations are provided for only three unknowns.

For each of the recorded images based on the combination of which the processor 108 may generate an output image, the system may determine the image's phase angle. In this regard, the processor 108 may assign to one of the images, e.g., the first of the images, a phase angle of 0°, regardless of the corresponding grid position, since the phase angles may correspond to the phase shift between the images, without consideration of the movement of the grid lines with respect to an external object, i.e., the image phases are measured relative to one another. The processor 108 may then calculate the respective phase angles of the remaining images, representing a phase shift from the phase of the image assigned a phase angle of 0°. For determining the phase angles, the images may be taken of light reflected from a substantially uniform surface. For example, if an object that does not have a substantially uniform surface is to be imaged, insertion into the camera's line of sight of a different object having a substantially uniform surface may be required for determining the phase angles.

In an embodiment of the present invention, the processor 108 may calibrate the actuator 110 to move the grid 102 so that the phase angles are set to predetermined phase angles, e.g., phase angles of 0°, 120°, and 240°. To calibrate the actuator 110, the processor 108 may cause the camera 106 to repeatedly record a set of images. For each of the images of the set, the processor 108 may separately determine the respective image phase angles and compare them to the predetermined phase angles. Based on a deviation of the determined actual phase angles from the predetermined phase angles, the processor 108 may output new voltage values in accordance with which voltages may be applied to the actuator 110 for moving the grid 102. This cycle, i.e., applying voltages to the actuator 110, capturing a set of images, separately determining the phase angles of the images of the set, comparing the determined phase angles to the predetermined phase angles, and outputting new voltage values may be repeatedly performed until the determined actual phase angles match the predetermined phase angles within a predetermined tolerance range. If there is a match, the processor 108 may conclude the calibration without changing the voltage values. The calibration may be performed quickly since for each cycle the phase angles of the images recorded by the camera 106 are directly determined.

Subsequent to calibration, the processor 108 may generate an output image of an object, e.g., in response to a user instruction, by causing the camera 106 to record three images and setting the value of each pixel of the output image according to the formula $I_P = \alpha \sqrt{(I_1-I_2)^2 + (I_2-I_3)^2 + (I_3-I_1)^2}$.

Figure 4:
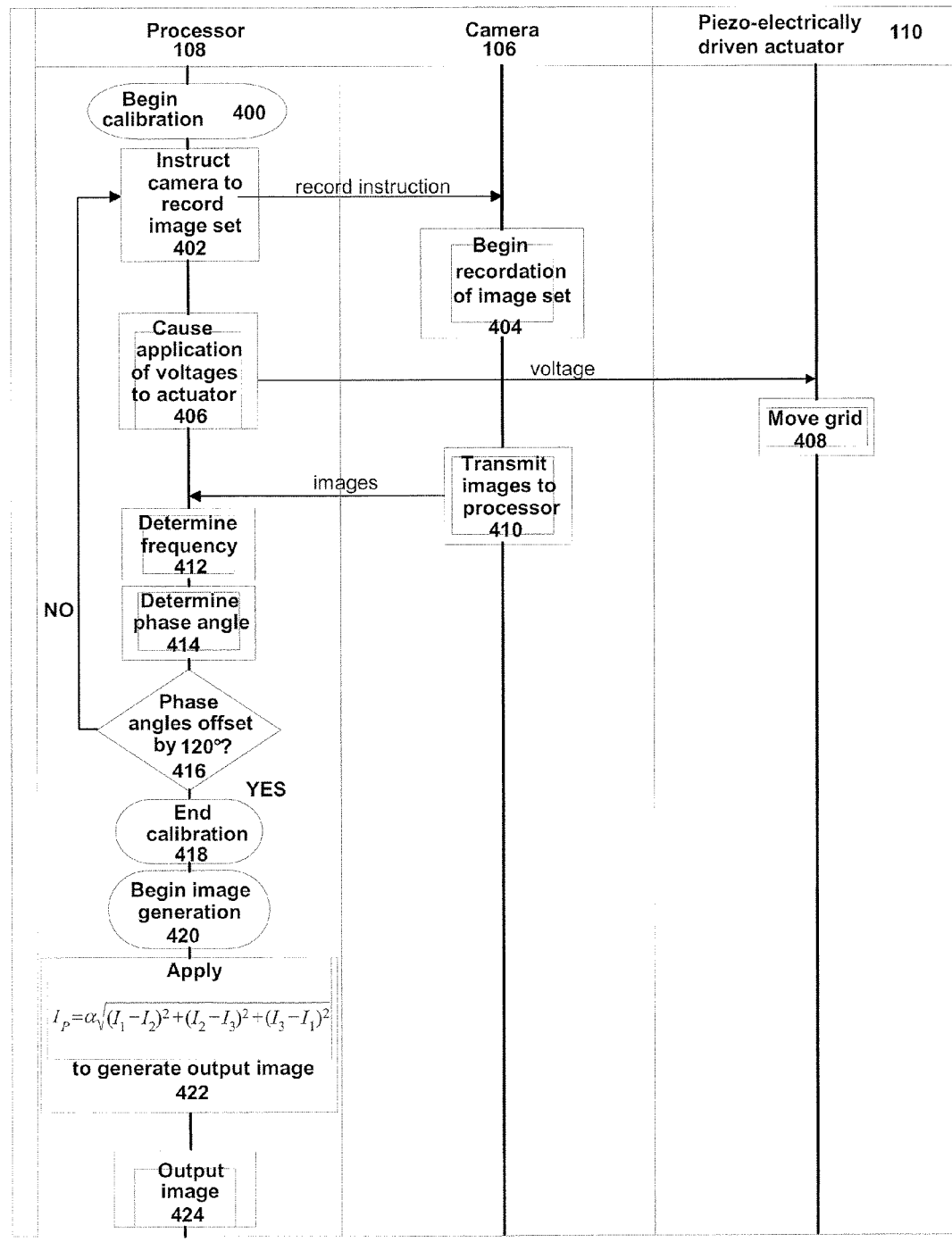
FIG. 4 is a flowchart and data flow diagram that illustrates a procedure for generating an optical section image according to an example embodiment of the present invention.

FIG. 4 is a flowchart that illustrates a procedure, e.g., which may be performed by the processor 108, camera 106, and actuator 110 as shows by the headings of FIG. 4, for obtaining an image according to this embodiment of the present invention. For example, the procedures of FIGS. 4, 6, 12, and 13, may be performed by execution of an algorithm, software, or equation stored as computer-executable instructions on a computer-readable medium in the processor 108, a memory 312, or any other part of the imaging system known to those of ordinary skill in the art. The computer-readable medium may include a floppy disk, optical disc, digital video disk, computer disk read only memory (CD-ROM) and the like. At 400, a calibration procedure may begin. At 402, the processor 108 may instruct the camera 106 to record of an image set, e.g., of three images. At 404, the camera may begin recordation of the image set. Between recordation of images of the set, the processor 108 may, at 406, cause the application of voltages to the peizo-electrically driven actuator 110. In response to the voltages, the actuator 110 may, at 408, move the grid 102. After recordation of the images, the camera 106 may, at 410, transmit the recorded images to the processor 108. It will be appreciated that the camera 106 may transmit each image after its recordation or may otherwise transmit them in a single batch transfer. At 414, the processor 108 may separately determine the image phase angle of each of the images. If the processor determines at 416 that the phase angles are not offset by 120°, the processor 108 may continue the calibration procedure. Otherwise, the processor 108 may end the calibration procedure at 418.

Subsequent to calibration, the processor 108 may begin an image generation procedure at 420 for an output image, e.g., in response to a user instruction. For the image generation procedure, 402-410 may be initially performed. Re-performance of 402-410 may be omitted if the object to be imaged provides sufficient data to determine image phase angles. In this regard, if an object to be imaged is itself of a uniform surface, such as a mirror, then the calibration may be performed using the object to be imaged. Accordingly, the processor 108 may use image data used in the calibration procedure for the image generation procedure. Further, even if the object to be imaged is of a non-uniform surface, it may occur that the data obtained from an image of the object is sufficient for the calibration procedure. By calculating the angular frequency (discussed in detail below) and phase angle for each image, the calculation results may be compared. If the results substantially match, it may be assumed that the object has provided sufficient data, i.e., imaging of a calibration slide having particular properties may be omitted. Since an object to be imaged often provides insufficient data for determining phase angle, a separate recordation of a designated object may be performed for phase angle determination. Then, at 422, the processor 108 may apply the formula $I_P = \alpha \sqrt{(I_1-I_2)^2 + (I_2-I_3)^2 + (I_3-I_1)^2}$ to each pixel to generate an output image, which the processor 108 may output at 424. The image may be output via any conventional output device, such as a computer screen, projector, and/or printer.

In an alternative embodiment of the present invention, calibration may be omitted. According to this embodiment, the processor 108 may cause the camera to record a single set of images of an object having a substantially uniform surface to determine the phase angles of the images caused by movement of the grid 102. The processor 108 may save the determined phase angles in a memory 312. Alternatively, if the object to be imaged has a uniform surface or includes substantial detail so that substantial data may be obtained from an image of the object, the processor 108 may determine the image phase angles from images of the object to be imaged, without previous imaging of another object that is inserted into the camera's line of sight solely for determining image phase angles.

Subsequent to the saving of the determined phase angles in the memory 312, the processor 108 may generate an output image of an object, e.g., in response to a user instruction, by causing the camera 106 to record three images and setting the value of each pixel of the output image to a value obtained by plugging in the saved phase angles into an equation matrix and solving for the $I_c$ and $I_s$ components of the pixel value. As discussed above, for each of the three images, a particular pixel value is $I_n = I_w + I_c \cos \phi_n + I_s \sin \phi_n$. Accordingly, a particular pixel may be defined as:

$$I_1 = I_w + I_c \cos\phi_1 + I_s \sin\phi_1$$
$$I_2 = I_w + I_c \cos\phi_2 + I_s \sin\phi_2 \quad \text{or} \quad \begin{bmatrix} I_1 \\ I_2 \\ I_3 \end{bmatrix} = \begin{bmatrix} 1 & \cos\phi_1 & \sin\phi_1 \\ 1 & \cos\phi_2 & \sin\phi_2 \\ 1 & \cos\phi_3 & \sin\phi_3 \end{bmatrix} \begin{bmatrix} I_w \\ I_c \\ I_s \end{bmatrix}.$$
$$I_3 = I_w + I_c \cos\phi_3 + I_s \sin\phi_3$$

The equation matrix may be re-expressed to solve for the variables $I_w$, $I_c$, and $I_s$, as follows:

$$\begin{bmatrix} I_w \\ I_c \\ I_s \end{bmatrix} = \begin{bmatrix} 1 & \cos\phi_1 & \sin\phi_1 \\ 1 & \cos\phi_2 & \sin\phi_2 \\ 1 & \cos\phi_3 & \sin\phi_3 \end{bmatrix}^{-1} \begin{bmatrix} I_1 \\ I_2 \\ I_3 \end{bmatrix}.$$

Figure 5:
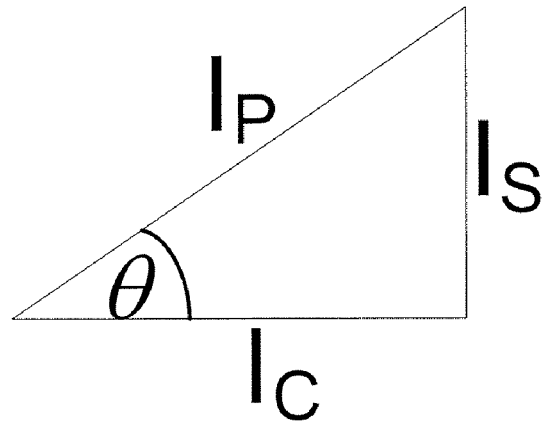
FIG. 5 illustrates the relationship of in-phase and quadrature components of a pixel value to an output image pixel value used for determining the output image pixel value according to an example embodiment of the present invention.

Once $I_c$ and $I_s$ are calculated, the processor 108 may determine the pixel value $I_p$ of the output image since $I_c$ and $I_s$ are the in-phase and quadrature in focus components of the pixel value $I_p$, as shown in FIG. 5. ($I_W$ is the widefield image). The processor 108 may determine the pixel value $I_p$ according to the formula $I_p = \sqrt{I_c^2 + I_s^2}$ (the Pythagorean theorem). While the values of the pixels $I_1$, $I_2$, and $I_3$ may be in part based on the grid lines projected onto the object, the value of $I_p$ (determined based on the components $I_c$ and $I_s$) is based entirely on the object and not on the grid lines projected onto the object. Further, because of the precise or substantially precise determination of the phase angles, the image generated by a combination of the pixel values $I_p$ determined according to the preceding equation does not include an artefact.

Figure 6:
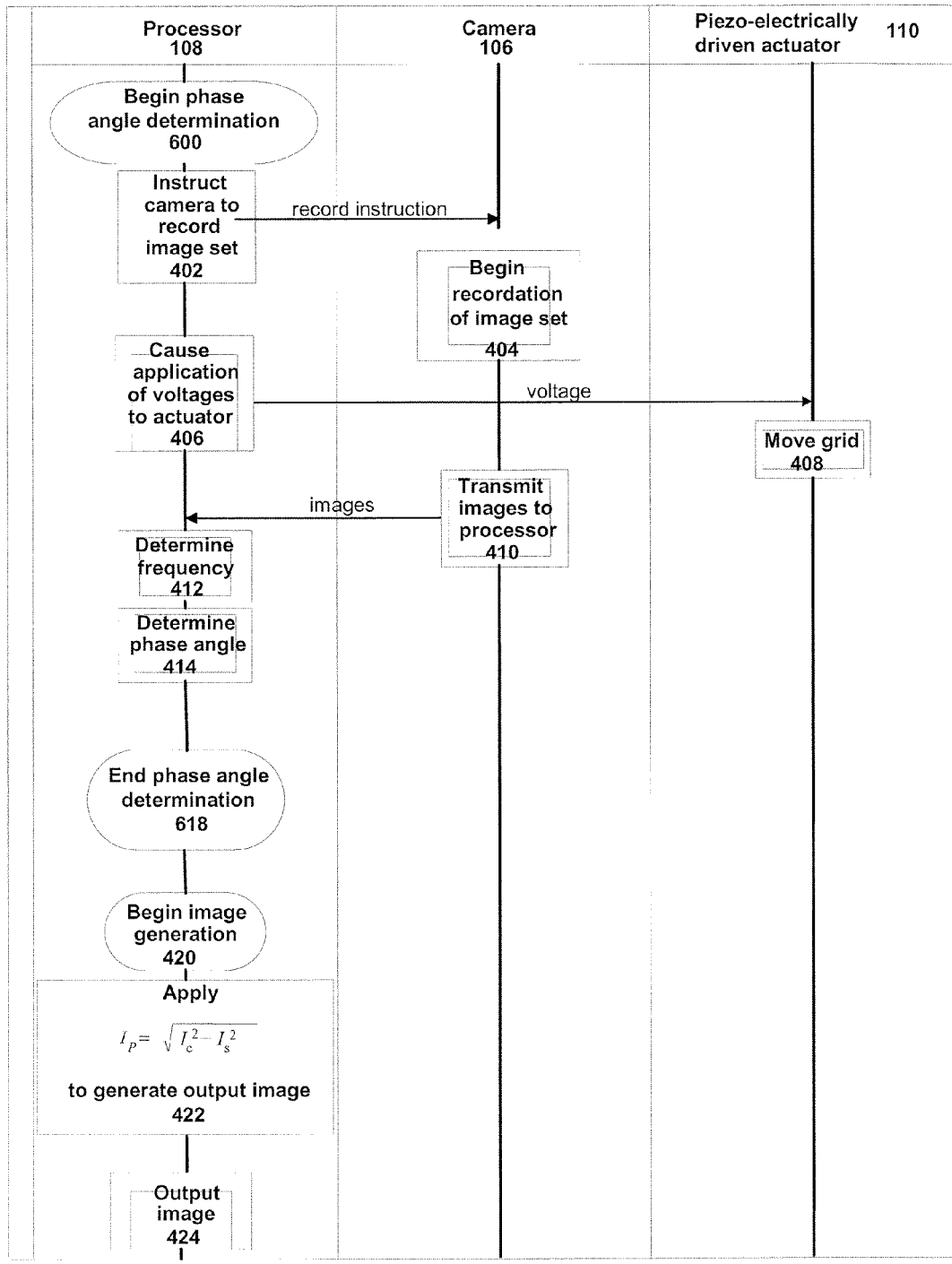
FIG. 6 is a flowchart and data flow diagram that illustrates a second procedure for generating an optical section image according to an optical section image according to an example embodiment of the present invention.

FIG. 6 is a flowchart that illustrates a procedure, e.g., which may be performed by the processor 108, camera 106, and actuator 110 as shows by the headings of FIG. 4, for obtaining an image according to this embodiment of the present invention. Elements of FIG. 6 which are described above with respect to FIG. 4 are provided with the same reference numerals. According to this embodiment, calibration is not performed. Instead, a phase angle determination procedure alone is performed. 400 and 418 are therefore replaced with 600 and 618, and the determination of 416 is not performed. With respect to 420, re-performance of 402-410 may be omitted if the object to be imaged provides sufficient data to determine image phase angles, as discussed above. Further, since calibration for obtaining phase angles offset by 120° is not performed according to this embodiment, 422 is replaced with 522 at which the formula $I_p = \sqrt{I_c^2 + I_s^2}$ is applied to generate an output image.

It will be appreciated that even according to the embodiment in which the calibration procedure is performed, the processor 108 may calculate output image pixels using the formula $I_p = \sqrt{I_c^2 + I_s^2}$. It will be appreciated that even according to the second embodiment, if the processor 108 determines, at 414, that the image phase angles are 0°, 120°, and 240°, the processor 108 may calculate output image pixels using the formula $I_P = \alpha\sqrt{(I_1-I_2)^2 + (I_2-I_3)^2 + (I_3-I_1)^2}$.

Accordingly, by determining the phase angle of the three images, the calibration may be performed quickly. Further, by determining the phase angle, an output image may be generated based on a set of images at different phase angles even without calibrating the actuator 110 to cause the grid lines of the images of the set to be at predetermined phase angles.

Referring to FIGS. 4 and 6, in an embodiment of the present invention, the processor 108 may determine, at 412, an angular frequency of the grid lines of the images of the image set, and may calculate a phase angle of an image of the set based on a correlation of the pixel values of the image to the determined frequency, as discussed below. Referring specifically to FIG. 4, while, in one embodiment of the present invention, 412 may be performed during each iteration of the calibration procedure for quality control by comparison of determined frequencies, in an alternative embodiment, 412 may be omitted during each iteration of the calibration procedure other than the first iteration, since once the frequency is known, it need not be recalculated. It will be appreciated that the frequency is not fixed. For example, the frequency may be dependent upon magnification of the reflected image or light reflected onto the object, which may depend on a position of a lens. To calculate a phase angle by correlation of pixel values to a determined frequency, it may be required for the frequency determination to be highly accurate. For example, use of FFT may be inadequate for the determination of the frequency. In an example embodiment of the present invention, the processor 108 may estimate the frequency with high accuracy using Bayesian Spectral Analysis, which will be recognized by those skilled in the art as an analysis that provides more fluid results than the discrete value results obtained using FFT.

For application of Bayesian Spectral Analysis, signal data of an image may be collected. Each signal may represented by an equation relating to a sinusoidal variation of image intensity. The equation may be $f(y_i) = r \cos(\omega y_i + \phi) + c$, where r is the magnitude, $\omega$ is the determined angular frequency, y is the pixel location, $\phi$ is the phase angle, and c is the mean of the image intensity. Regarding y, it will be appreciated that this may be either the pixel coordinate in the vertical direction or in the horizontal direction, depending on the orientation of the grid lines. For example, the orientation of the grid 102 may be such that the grid lines are projected horizontally onto the image, thereby causing variation of image intensity in the vertical direction. In this instance, the pixel coordinates may be those in the vertical direction. The sinusoidal variation of image intensity may also be represented by $f(y_i) = a \cos \omega y_i + b \sin \omega y_i + c$, where a and b are the cosine and sine components of the magnitude. While the preceding two equations may be equivalent, the former equation includes only both of the two unknowns $\omega$ and $\phi$, while the latter includes only one of the two unknowns, i.e., $\omega$. Accordingly, using the latter formula, the angular frequency $\omega$ may be determines via Bayesian Spectral Analysis, e.g., in the following manner.

Applying the latter formula to a plurality of data samples 'd', the following matrix formulation may be obtained:

$$\begin{bmatrix} d_1 \\ d_2 \\ d_3 \\ \vdots \\ d_N \end{bmatrix} = \begin{bmatrix} \cos\omega y_1 & \sin\omega y_1 & 1 \\ \cos\omega y_2 & \sin\omega y_2 & 1 \\ \cos\omega y_3 & \sin\omega y_3 & 1 \\ & \vdots & \\ \cos\omega y_N & \sin\omega y_N & 1 \end{bmatrix} \begin{bmatrix} a \\ b \\ c \end{bmatrix} + \begin{bmatrix} e_1 \\ e_2 \\ e_3 \\ \vdots \\ e_N \end{bmatrix}.$$

A matrix may thus be obtained, where:

$$G = \begin{bmatrix} \cos\omega y_1 & \sin\omega y_1 & 1 \\ \cos\omega y_2 & \sin\omega y_2 & 1 \\ \cos\omega y_3 & \sin\omega y_3 & 1 \\ & \vdots & \\ \cos\omega y_N & \sin\omega y_N & 1 \end{bmatrix}.$$

The linear coefficients and the noise standard deviation may be integrated out. The frequency may then be obtained by applying the G matrix to the Bayesian formula $$p(\omega \mid d, I) \propto \frac{[d^T d - d^T G(G^T G)^{-1} G^T d]^{\frac{M-N}{2}}}{\sqrt{\det(G^T G)}},$$

or determining a probable value of the angular frequency ω given the data set d. M is the number of columns included in the G matrix. Samples of a single one of the images may be sufficient for determining the frequency. However, increased accuracy may be obtained by inputting data of more than one image.

In one example embodiment of the present invention, a narrow strip of the image may be used as the data source, rather than the entire image. For example, if the grid lines are projected horizontally onto the image, causing variation of image intensity in the vertical direction, a vertical strip of the image may be used as the data source. While use of a narrow strip may provide less data for input into the equation than if the entire image is used, it may increase accuracy since the grid lines may be projected at an angle with respect to an imaging area, thereby skewing the data input, as discussed in detail below.

In an alternative embodiment of the present invention, for the data used as input to the Bayesian Spectral Analysis, values of all of the image's pixels may be used.

In yet another embodiment, each row of pixels (or column of pixels if the grid lines are projected vertically) may be summed. The pixel value sums $$\sum_{l=1}^{n} l.$$

for each row may be used as the data input for the Bayesian Spectral Analysis, as though the sums are actual pixel values of a narrow vertical strip that is one pixel wide, i.e., one value per row. The latter two embodiments may provide greater accuracy in the measurement of the frequency than does the former embodiment since it may occur that some of the recorded pixel values are incorrect, e.g., due to noise. Therefore, the more pixel values considered, the more accurate the frequency estimation may be.

Figure 7:
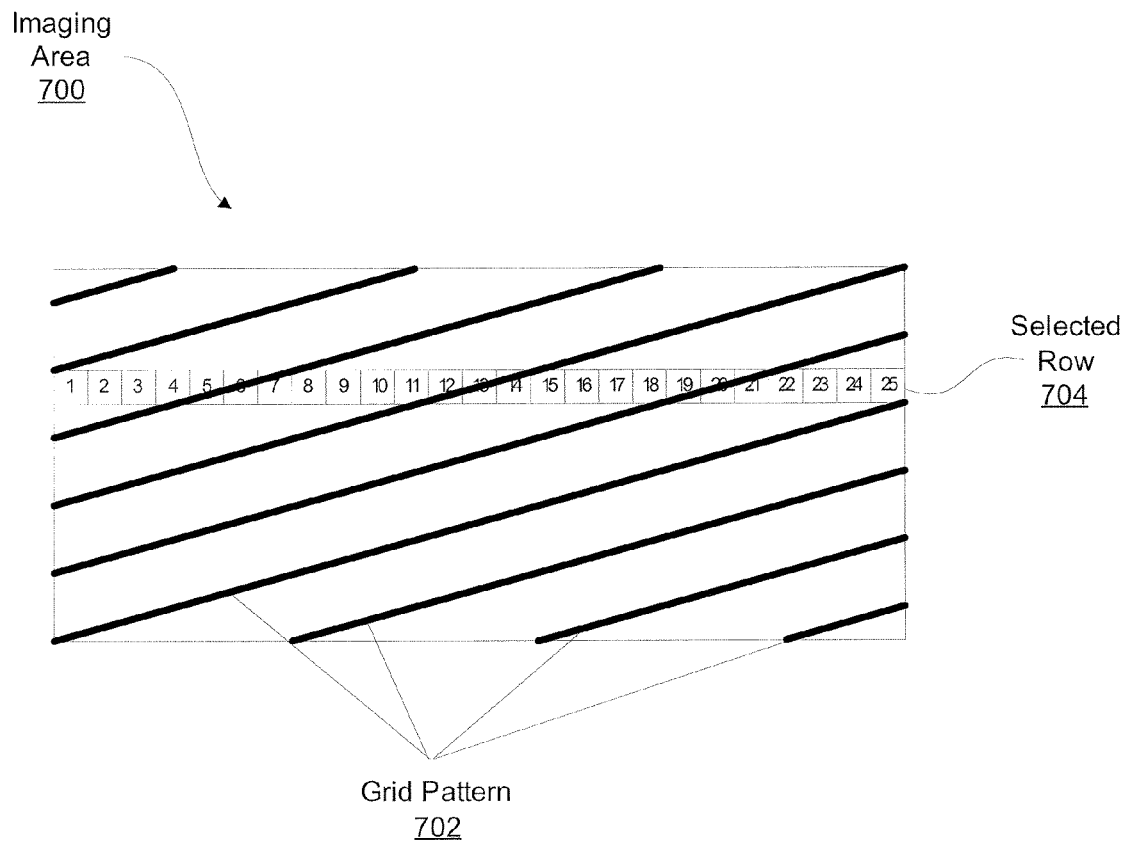
FIG. 7 illustrates an example imaging area having a grid pattern that differently affects pixels of a same pixel row.

However, with respect to the latter two embodiments, if the grid 102 is positioned such that the grid lines are projected at an angle with respect to an imaging area, the sinusoidal variation of the image intensity caused by the projected grid pattern may unequally affect pixels along the same row, as indicated above. FIG. 7 illustrates this phenomenon. FIG. 7 shows an imaging area 700 onto which is projected a grid pattern 702 at an angle. With respect to a selected row 704, the grid pattern 702 may differently affect values of different pixels of the row 704. For example, while pixel 2 is shown to be unaffected, pixel 13 is shown to be greatly affected. Accordingly, if the pixel values of the selected row 704 are summed or otherwise used in combination as data input for the frequency determination, the obtained frequency value may be incorrect.

Therefore, in an example embodiment of the present invention, prior to determining the frequency of the grid pattern, the image may be rotated so that the grid pattern is parallel to the abscissa (or to the ordinate if the grid lines are projected vertically) of the imaging area. An angle (α) at which the grid lines are projected with respect to the abscissa may be determined, and the image may be rotated by −α.

In an embodiment of the present invention, the angle in radians at which the grid lines are projected with respect to the abscissa of the imaging area may be determined by (a) determining a frequency of the grid pattern along two arbitrary diagonals superimposed onto the image and disposed at opposite angles, 45° and −45°, with respect to the abscissa of the imaging area, and (b) applying the determined frequencies to the formula $$\arctan\left(\frac{F_1 - F_2}{F_1 + F_2}\right),$$

where $F_1$ is the determined frequency along one of the diagonals and $F_2$ is the determined frequency along the other of the diagonals. The tilt angle α may be obtained by application of the preceding formula when the diagonals are disposed at 45° and −45°, since tan(45°)=1 and since $$\tan(\alpha) * \tan([\text{diagonal angle}]) = \frac{F_1 - F_2}{F_1 + F_2}.$$

Thus, where the diagonal angle is 45°, $$\tan(\alpha) = \frac{F_1 - F_2}{F_1 + F_2}.$$

For determining the frequencies along a diagonal, values of a strip of pixels along the selected diagonal may be input into a frequency determining formula as discussed above, e.g., they may be used as input to the Bayesian Spectral Analysis.

Figure 8:
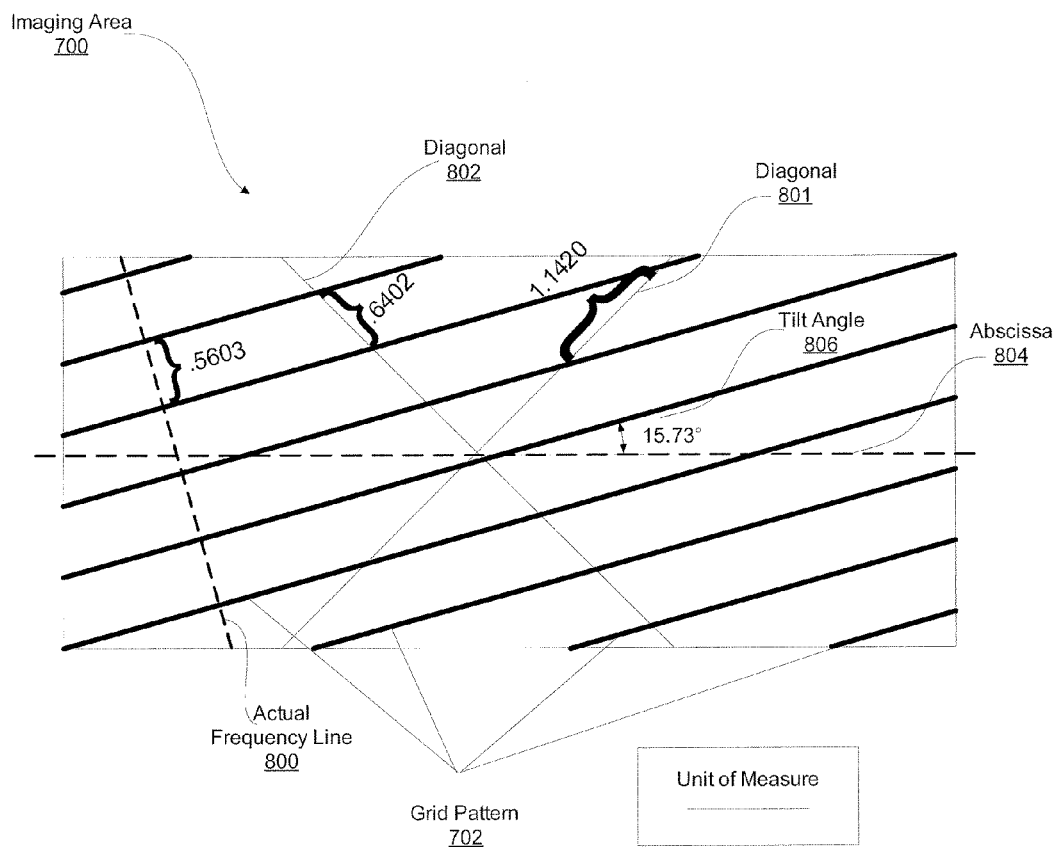
FIG. 8 illustrates a set of frequencies that may be used for determining a grid pattern tilt, according to an example embodiment of the present invention.

For example, FIG. 8 shows a diagonal 801 drawn at a 45° angle and a diagonal 802 drawn at a −45° angle with respect to the abscissa of the imaging area 700. When the grid pattern is arranged at an angle, the actual frequency of the grid lines may be different than their frequencies taken along the diagonals. Further, the frequencies taken along the two diagonals may differ. For example, the grid line frequency taken along an actual frequency line 800, representing the actual grid frequency in FIG. 8 is approximately 0.5603 with respect to the unit of measure in FIG. 8. However, the grid line frequencies measured along the diagonals 801 and 802 are approximately 1.1420 and 0.6402 with respect to the unit of measure, respectively.

Applying these frequencies to the formula $$\arctan\left(\frac{F_1 - F_2}{F_1 + F_2}\right),$$

it may be determined that the grid tilt angle in radians with respect to the abscissa 804 in FIG. 8 is approximately $$\arctan\left(\frac{1.1420 - .6402 = .5018}{1.1420 + .6402 = 1.7822} = .2816\right) = .2745\,(15.73°).$$

It is noted that FIG. 8 shows the grid line periods of the diagonals 801 and 802 and of the actual frequency line 800. However, conversion of the periods to angular frequency by $$\frac{2\pi}{period}$$

yields the same result. For example, for the period 1.1420, the angular frequency is 5.50191358, and for the period 0.6402, the angular frequency is 9.81441004. Substituting the periods for these frequencies in the equation $$\arctan\left(\frac{F_1 - F_2}{F_1 + F_2}\right)$$

similarly yields a tilt angle of 15.73°. The image may be tilted by −15.73, using any suitably appropriate procedure, so that the grid lines may be parallel to the abscissa 804.

Once the tilt is corrected, the system and method may determine the grid line frequency in the manner discussed above.

Figure 9:
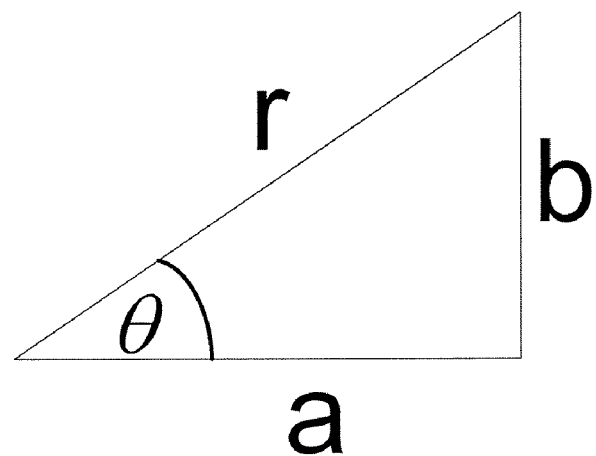
FIG. 9 illustrates the relationship of the components r, a, b, and phase angle, where a and b are, respectively, the cosine and sine components of the magnitude.

Once the frequency is determined, the phase angle of an image may be determined. For a pixel value of the image, the a and b components of a cos ωy$_i$+b sin ωy$_i$+c may be estimated by using linear regression of the pixel value to the determined frequency. Once a and b are estimated, the phase angle of the image may be calculated as arctan $$\left(\frac{b}{a}\right)$$

according to the relationship shown in FIG. 9. The determination of a phase angle of any single image may be performed without data regarding the other images of the set. For example, referring to FIGS. 4 and 6, 412 and 414 may be performed as soon as an image is received from the camera 106, even if the camera 106 transmits each image separately immediately subsequent to its recordation. Accordingly, while the actuator 110 moves the grid 102 for preparation of recordation of a subsequent image and/or while the camera 106 records a subsequent image, the processor 108 may perform 412 and 414 for a previously received image.

Use of More than Three Images

Figure 10:
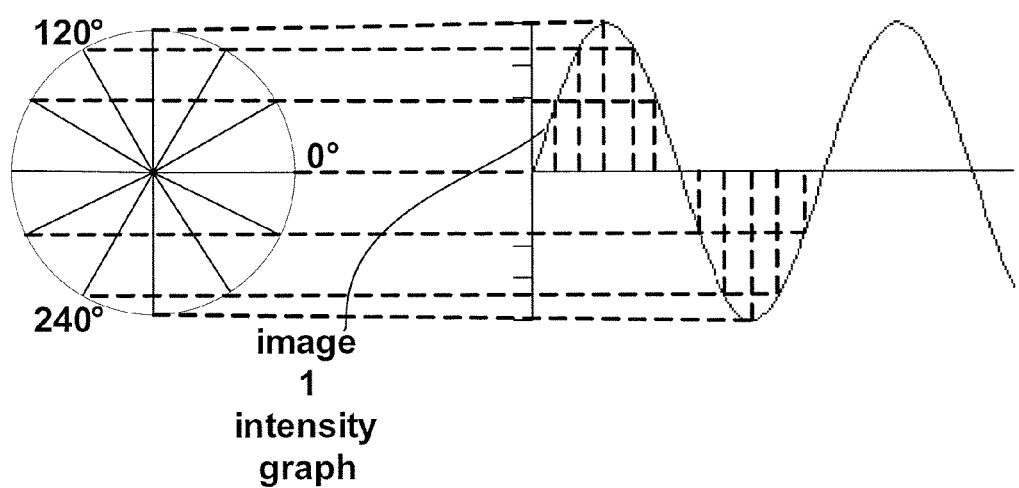
FIG. 10 illustrates phase angles of more than three images used for generating an output image according to an example embodiment of the present invention.

As discussed in detail above, the image generation procedure may be performed by determining a pixel value based on a combination of corresponding pixel values of a set of images, where for each image grid lines are projected at a different phase angle. While three images are conventionally included in a set of images used to generate an output image, in an embodiment of the present invention, to obtain a better quality image, the processor 108 may generate an output image based on pixel values of more than three images. For example, the offset between phase angles may be decreased as shown in FIG. 10. FIG. 10 shows a 30° phase angle offset between images. For clarity, only the intensity graph of a single image, i.e., the reference image, is shown. The dashed lines indicate the start of other image intensity graphs. According to this embodiment, the matrix formulation $$\begin{bmatrix} I_1 \\ I_2 \\ I_3 \end{bmatrix} = \begin{bmatrix} 1 & \cos\phi_1 & \sin\phi_1 \\ 1 & \cos\phi_2 & \sin\phi_2 \\ 1 & \cos\phi_3 & \sin\phi_3 \end{bmatrix} \begin{bmatrix} I_w \\ I_c \\ I_s \end{bmatrix}$$

may be replaced with $$\begin{bmatrix} I_1 \\ \vdots \\ I_M \end{bmatrix} = \begin{bmatrix} 1 & \cos\phi_1 & \sin\phi_1 \\ \vdots & & \\ 1 & \cos\phi_M & \sin\phi_M \end{bmatrix} \begin{bmatrix} I_w \\ I_c \\ I_s \end{bmatrix}.$$

With determination of the phase angles as discussed above, a set of more than three images provides more equations than unknowns, since only $I_w$, $I_c$, and $I_s$ are unknown. It may be that the equations do not completely agree because of noise. Accordingly, a regression analysis, e.g., least squares regression, may be applied for $I_w$, $I_c$, and $I_s$, which may reduce the noise present in the signals. In particular, the following least squares regression formula may be applied:

$$\begin{bmatrix} I_w \\ I_c \\ I_s \end{bmatrix} = (G^T G)^{-1} G^T \begin{bmatrix} I_1 \\ I_2 \\ I_3 \\ \vdots \\ I_M \end{bmatrix}, \text{ where } (G^T G)^{-1} = \begin{bmatrix} \frac{1}{M} & 0 & 0 \\ 0 & \frac{2}{M} & 0 \\ 0 & 0 & \frac{2}{M} \end{bmatrix},$$

$$G = \begin{bmatrix} 1 & \cos\phi_1 & \cos\phi_1 \\ \vdots & & \\ 1 & \cos\phi_M & \sin\phi_M \end{bmatrix},$$

and $G^T$ is the transpose of G. This formula may be applied even if only three images are used.

If the phase angles of each pair of successive ones of the more than three images are offset by an equal number of degrees, other formulae may be applied. Regardless of the number of images (M) of the set, $I_w$, $I_c$, and $I_s$ may be calculated as:

$$I_w = \frac{1}{M} \sum_{k=0}^{M-1} I_{k+1}$$

$$I_c = \frac{2}{M} \sum_{k=0}^{M-1} I_{k+1} \cos\left(\frac{2\pi k}{M}\right)$$

$$I_s = \frac{2}{M} \sum_{k=0}^{M-1} I_{k+1} \sin\left(\frac{2\pi k}{M}\right).$$

This formula may be applied even where M=3. Once $I_c$ and $I_s$ are calculated using either of the preceding two formulae, $I_p$ may be calculated using the formula $I_p = \sqrt{I_c^2 I_s^2}$. Further, if four images are used and phase angles of each pair of successive ones of the four images are offset by an equal number of degrees, $I_p$ may be calculated using the formula $I_p = \alpha \sqrt{(I_1 - I_3)^2 + (I_2 - I_4)^2}$.

In an embodiment of the present invention, the pixel values of the generated image may be recursively updated to account for newly obtained images by modifying the least squares solution according to conventional procedures for updating a least squares solution. For example, a recursive least squares formula may include conventionally used formulae, such as the Sherman-Morrison Formula or the Woodbury Formula. Accordingly, after an image based on pixel data of three or more images is output, a user may instruct the processor 108 to generate a more enhanced image. In response, the processor 108 may obtain a newly recorded image (including a grid pattern) and may update the already calculated values of $I_c$ and $I_s$, without re-performing the calculation using the images previously used. Accordingly, it is not required for the images previously used to be stored in case an update is desired.

Preprocessing

Conversion of Pixel Data for Estimating Parameters

Figure 11A:
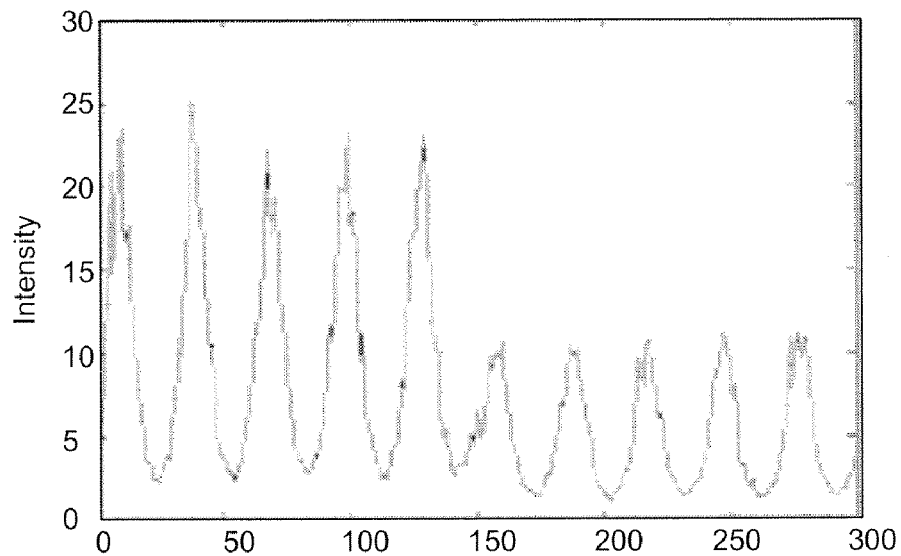
FIGS. 11*a* and 11*b* show a difference between a sinusoidal variation of image intensity of an untransformed image and an image that is transformed according to an embodiment of the present invention.
Figure 11B:
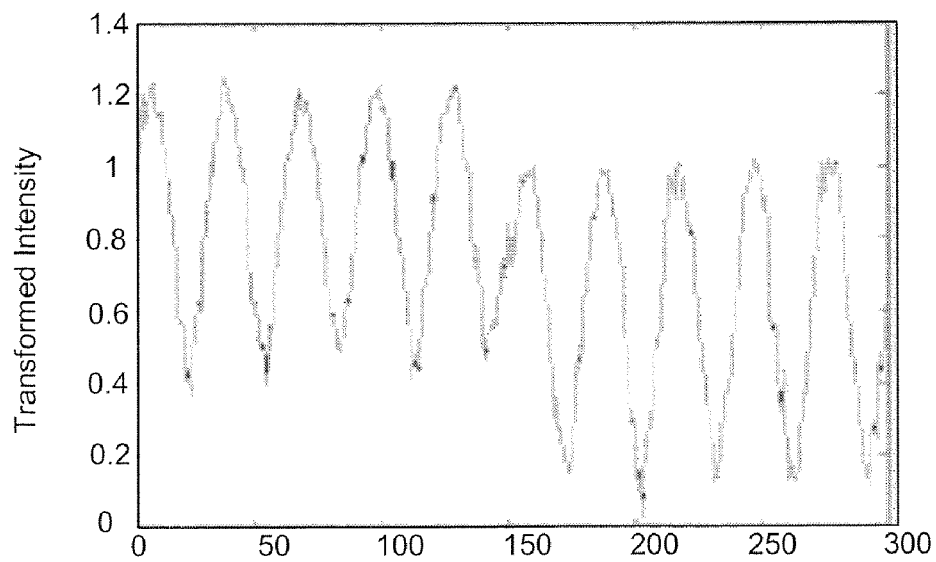

The pixel values of an image returned by the camera 106 often provide a non-uniform sinusoidal variation in image intensity. Accordingly, calibration of the actuator 110 to provide for particular phase angles, whether based on measurement with FFT of an artefact or based on direct calculation of phase angles, and/or calculation of phase angles for generating an output image based on $I_p = \sqrt{I_c^2 + I_s^2}$, may be faulty if based on pixel values recorded by the camera 106. In an embodiment of the present invention, the system may substitute each recorded pixel value used for calibration or for determining phase angles (and/or frequency) with a value obtained by a logarithmic or approximately logarithmic conversion of the pixel value. The resultant values may provide a more uniform sinusoidal variation in image intensities. FIG. 11 shows a difference between the sinusoidal variation of image intensity of an untransformed image and a transformed image. Whereas the amplitude of the sine wave in graph (a), which represents the image intensity of an untransformed image, is substantially non-uniform, the amplitude of the sine wave in graph (b), which represents the image intensity of a transformed image, is substantially more uniform.

Subsequent to the conversion, either conventional calibration or calibration according to directly calculated phase angles, may be performed. Alternatively, the phase angles may be calculated without calibration as discussed in detail above. Subsequent to calibration and/or calculation of the phase angles, the processor 108 may generate an output image based on the untransformed, i.e., originally recorded, pixel values according to the procedures discussed in detail above.

In one embodiment of the present invention, for conversion of the recorded pixel values, a simple transformation of each pixel to its logarithmic value may be performed. According to this embodiment, an adverse effect may be realized where noise at low image intensity is amplified, distorting the image intensity values. In an alternative embodiment, an inverse hyperbolic sine function $$\sinh^{-1}\left(\frac{x}{2}\right)$$

may be used for each pixel, where x is the originally recorded image intensity value. The latter function approximates the function log(x) to base 'e' (natural logarithms) with respect to large pixel values, but not for smaller values. According to this embodiment, amplification of noise at low image intensities may be avoided. It will be appreciated that the transformation of pixel values may be performed using any function that smoothens the amplitudes of the sinusoidal variations in intensity across an image.

Postprocessing

Removal of Artefact from Output Image

Regardless of the preciseness of the calibration procedure or the determination of the phase angles, the output image obtained by combining the three or more images may include an artefact. The artefact may be a sinusoidal variance in image intensity similar to the grid pattern. The sinusoidal variance of the artefact may be a product of the grid pattern and may be at some harmonic of the grid pattern's sine wave. In particular, it may be assumed that the sinusoidal variance of the artefact is within three harmonics of the grid pattern frequency.

In an example embodiment of the present invention, the system and method may remove the sinusoidal variance of image intensity caused by the artefact from the output image.

In one example embodiment of the present invention, the sine wave representing the sinusoidal variation in image intensity due the artefact may be determined. The determined sine wave may be subtracted from the image, resulting in an image without the artefact. A pixel value of the output image may be represented by Q=I+B, where Q is the pixel value, I is the portion of the pixel value contributed by the imaged object, and B is the portion of the pixel value contributed by the artefact. For each pixel value, the corresponding value of B may be determined and subtracted from Q to provide I, the pixel value without any artefact contribution.

As discussed in detail above, the sinusoidal variation in image intensity due to the projected grid pattern may be represented by $f(y_i) = a \cos \omega y_i + b \sin \omega y_i + c$. Similarly, B (the artefact contribution to the pixel value at row y, assuming a vertically projected grid pattern and artefact) may be represented by $a_1 \cos(\omega y_i) + b_1 \sin(\omega y_i) + a_2 \cos(2\omega y_i) + b_2 \sin(2\omega y_i) + a_3 \cos(3\omega y_i) + b_3 \sin(3\omega y_i)$. Each cos/sin set may correspond to an artefact. It may be assumed that the artefact is one or more of harmonics 1 to 3. Therefore, the system and method may assume that the equation above including the three cos/sin sets represents the artefact in the image, if any.

Therefore, a pixel value at a particular row $y_i$ may be represented by $Q(x, y_i) = I(x, y_i) + a_1 \cos(\omega y_i) + b_1 \sin(\omega y_i) + a_2 \cos(2\omega y_i) + b_2 \sin(2\omega y_i) + a_3 \cos(3\omega y_i) + b_3 \sin(3\omega y_i)$. For example, taking pixels along a vertical strip, their values may be represented by:

$$Q_1 = I_1 + a_1\cos(\omega 1) + b_1\sin(\omega 1) + a_2\cos(2\omega 1) +$$
$$b_2\sin(2\omega 1) + a_3\cos(3\omega 1) + b_3\sin(3\omega 1);$$
$$Q_2 = I_2 + a_1\cos(\omega 2) + b_1\sin(\omega 2) + a_2\cos(2\omega 2) +$$
$$b_2\sin(2\omega 2) + a_3\cos(3\omega 2) + b_3\sin(3\omega 2);$$
$$Q_3 = I_3 + a_1\cos(\omega 3) + b_1\sin(\omega 3) + a_2\cos(2\omega 3) +$$
$$b_2\sin(2\omega 3) + a_3\cos(3\omega 3) + b_3\sin(3\omega 3);$$
$$\vdots$$
$$Q_n = I_n + a_1\cos(\omega n) + b_1\sin(\omega n) + a_2\cos(2\omega n) +$$
$$b_2\sin(2\omega n) + a_3\cos(3\omega n) + b_3\sin(3\omega n).$$

These equations may be re-expressed in matrix form as q=b*G, where $$q = \begin{bmatrix} q_1 \\ q_2 \\ q_3 \\ \vdots \\ q_n \end{bmatrix},$$

-continued $$b = \begin{bmatrix} I \\ a_1 \\ b_1 \\ a_2 \\ b_2 \\ a_3 \\ b_3 \end{bmatrix}, \text{ and}$$

$$G = \begin{bmatrix} 1 & \cos(\omega y_1) & \sin(\omega y_1) & \cos(2\omega y_1) \\ \sin(2\omega y_1) & \cos(3\omega y_1) & \sin(3\omega y_1) \\ 1 & \cos(\omega y_2) & \sin(\omega y_2) & \cos(2\omega y_2) \\ \sin(2\omega y_2) & \cos(3\omega y_2) & \sin(3\omega y_2) \\ 1 & \cos(\omega y_3) & \sin(\omega y_3) & \cos(2\omega y_3) \\ \sin(2\omega y_3) & \cos(3\omega y_3) & \sin(3\omega y_3) \\ \vdots \\ 1 & \cos(\omega y_n) & \sin(\omega y_n) & \cos(2\omega y_n) \\ \sin(2\omega y_n) & \cos(3\omega y_n) & \sin(3\omega y_n) \end{bmatrix}.$$

Although, the value of I depends on the precise pixel location (x,y), this is unimportant for determining the sinusoidal variation of intensity that is a result of the artefact. Therefore, for the matrices above, I is multiplied by 1, regardless of the row.

The values of each component of this G matrix may be known if the angular frequency of the grid pattern is determined. Accordingly, the system and method may first determine the angular frequency as discussed above. For example, the pixel values may be input into a Bayesian Spectral Analysis. This may include rotation of the image to produce a grid pattern that is parallel to the abscissa and summation of values of pixels in each row, as discussed above with reference to FIG. 8. In an embodiment in which the angular frequency is determined for determining the phase angles, e.g., during calibration, the previously determined frequency may be plugged into the equation, without re-performing an angular frequency determination. In an embodiment in which the angular frequency is not determined prior to the postprocessing of the image, the system and method may perform the angular frequency determination for the postprocessing procedure. According to this embodiment, the system and method may retrieve stored pixel values of an input image to determine the angular frequency of the grid pattern and input the determined frequency into the G matrix, but may retrieve pixel values of the output image for input into the q matrix.

The values of a1, b1, a2, b2, a3, and b3 (of the b matrix) may therefore be determined by input of the above matrices into a regression analysis. For example, the following least squares regression formula may be applied using this G matrix:

$$\begin{bmatrix} I \\ a_1 \\ b_1 \\ a_2 \\ b_2 \\ a_3 \\ b_3 \end{bmatrix} = (G^T G)^{-1} G^T \begin{bmatrix} q_1 \\ q_2 \\ q_3 \\ \vdots \\ q_n \end{bmatrix},$$

where $G^T$ is the transpose of G. Although, one pixel sample per row (or column if the grid pattern is formed of vertical lines) is shown above, additional pixel samples per row (or column) may be input into the q matrix, and the G matrix may correspondingly include additional rows. Therefore a plurality of rows of the G matrix may refer to the same $\omega y_i$ value.

Once the values of the matrix b are determined, the values of:

$$a_1 \cos(\omega 1) + b_1 \sin(\omega 1) + a_2 \cos(2\omega 1) +$$
$$b_2 \sin(2\omega 1) + a_3 \cos(3\omega 1) + b_3 \sin(3\omega 1);$$

$$a_1 \cos(\omega 2) + b_1 \sin(\omega 2) + a_2 \cos(2\omega 2) +$$
$$b_2 \sin(2\omega 2) + a_3 \cos(3\omega 2) + b_3 \sin(3\omega 2);$$

$$a_1 \cos(\omega 3) + b_1 \sin(\omega 3) + a_2 \cos(2\omega 3) +$$
$$b_2 \sin(2\omega 3) + a_3 \cos(3\omega 3) + b_3 \sin(3\omega 3);$$

$$\vdots$$

$$a_1 \cos(\omega n) + b_1 \sin(\omega n) + a_2 \cos(2\omega n) +$$
$$b_2 \sin(2\omega n) + a_3 \cos(3\omega n) + b_3 \sin(3\omega n)$$

may be determined by b*G. These values may be the contributions of the artefact to the pixels. The reason for the difference of the contribution of the artefact at different rows, and therefore the different equation values at the different rows, may be due to the vertical sinusoidal variation in image intensity, where the grid pattern is vertically projected.

Once these values are determined, the values of the above equations may be subtracted from the output image pixel values. For example, for each pixel of row 1, the value of $a_1 \cos(\omega 1) + b_1 \sin(\omega 1) + a_2 \cos(2\omega 1) + b_2 \sin(2\omega 1) + a_3 \cos(3\omega 1) + b_3 \sin(3\omega 1)$ may be subtracted from the pixel value. For the sine wave subtraction phase, the system and method may assign each row to the same row number to which it was assigned when input into the regression analysis. For example, if for the regression analysis, pixels at a first row of the imaging area are assigned to a row labeled "row 1," then the value of $a_1 \cos(\omega 1) + b_1 \sin(\omega 1) + a_2 \cos(2\omega 1) + b_2 \sin(2\omega 1) + a_3 \cos(3\omega 1) + b_3 \sin(3\omega 1)$ may be subtracted from the pixels of the first row of the imaging area. Otherwise, the wrong values may be subtracted from each of the rows.

It may occur that an artefact in the output image is constructed of less than three harmonics of the grid pattern, in which case some parts of $a_1 \cos(\omega i) + b_1 \sin(\omega i) + a_2 \cos(2\omega i) + b_2 \sin(2\omega i) + a_3 \cos(3\omega i) + b_3 \sin(3\omega i)$ may equal 0. For example, if the artefact is only a first harmonic of the grid pattern, then $a_2 \cos(2\omega i) + b_2 \sin(2\omega i) + a_3 \cos(3\omega i) + b_3 \sin(3\omega i)$ may equal 0.

In one example embodiment of the present invention, 3 harmonics may always be assumed. In this instance, the regression analysis may yield values of $a_2$, $b_2$, $a_3$, and $b_3$ that are close to or equal to 0.

In another example embodiment of the present invention, instead of a 3 harmonic assumption, a number of harmonics of the grid pattern frequency that forms the artefact may be initially determined, according to conventional procedures for determination of a number of harmonics. The system and method may vary the matrix structure according to this determination. For example, if it is determined that the artefact includes components that are of two harmonics of the grid pattern frequency, then instead of the matrix structure discussed above, the system and method may input into the regression analysis an n×5 G matrix, instead of an n×7 matrix. The matrix may have the following structure:

$$G = \begin{bmatrix} 1 & \cos(\omega y_1) & \sin(\omega y_1) & \cos(2\omega y_1) & \sin(2\omega y_1) \\ 1 & \cos(\omega y_2) & \sin(\omega y_2) & \cos(2\omega y_2) & \sin(2\omega y_2) \\ 1 & \cos(\omega y_3) & \sin(\omega y_3) & \cos(2\omega y_3) & \sin(2\omega y_3) \\ \vdots & & & & \\ 1 & \cos(\omega y_n) & \sin(\omega y_n) & \cos(2\omega y_n) & \sin(2\omega y_n) \end{bmatrix}.$$

This matrix may provide for determining the a1, a2, b1, and b2 coefficients, without determination of the a3 and b3 coefficients, since the latter pair may be assumed to equal 0 based on the harmonics number determination. This may increase accuracy of the determination of the values of the former two coefficient pairs, since the regression analysis does not attribute any value to a fictional third coefficient pair.

In an example embodiment of the present invention, a narrow, e.g., vertical, strip of the output image may be used as the input for the q matrix. Alternatively, a greater portion of the image may be used. In one particular embodiment, sums of pixel values, e.g., per row, may be used as the input for the q matrix. In one particular embodiment of the present invention, the output image may be rotated so that the artefact, if any, is parallel to the abscissa of the imaging area, as discussed above with respect to the angular frequency determination and the grid pattern with reference to FIG. 8.

In an example embodiment of the present invention, instead of use of the actual output image pixel values for the q matrix, the system and method may use preprocessed output image pixel values for the q matrix. The output image pixel values may be preprocessed by a logarithmic or approximately logarithmic conversion of the pixel values for a more uniform sinusoidal variation in image intensities, as discussed above with reference to FIG. 11. Similarly, for grid pattern angular frequency determination for the G matrix, preprocessed pixel values of an input image may be used instead of the actual pixel values of the input image.

According to this embodiment, the artefact contribution, if any, to the output image may be subtracted from the preprocessed output image pixel values, rather than from the actual output image pixel values. Subsequent to the subtraction, the system and method may input the modified preprocessed pixel values into an equation for an inverse log transform to obtain modified actual output image pixel values, i.e., modified by removal of the artefact, if any.

Figure 12:
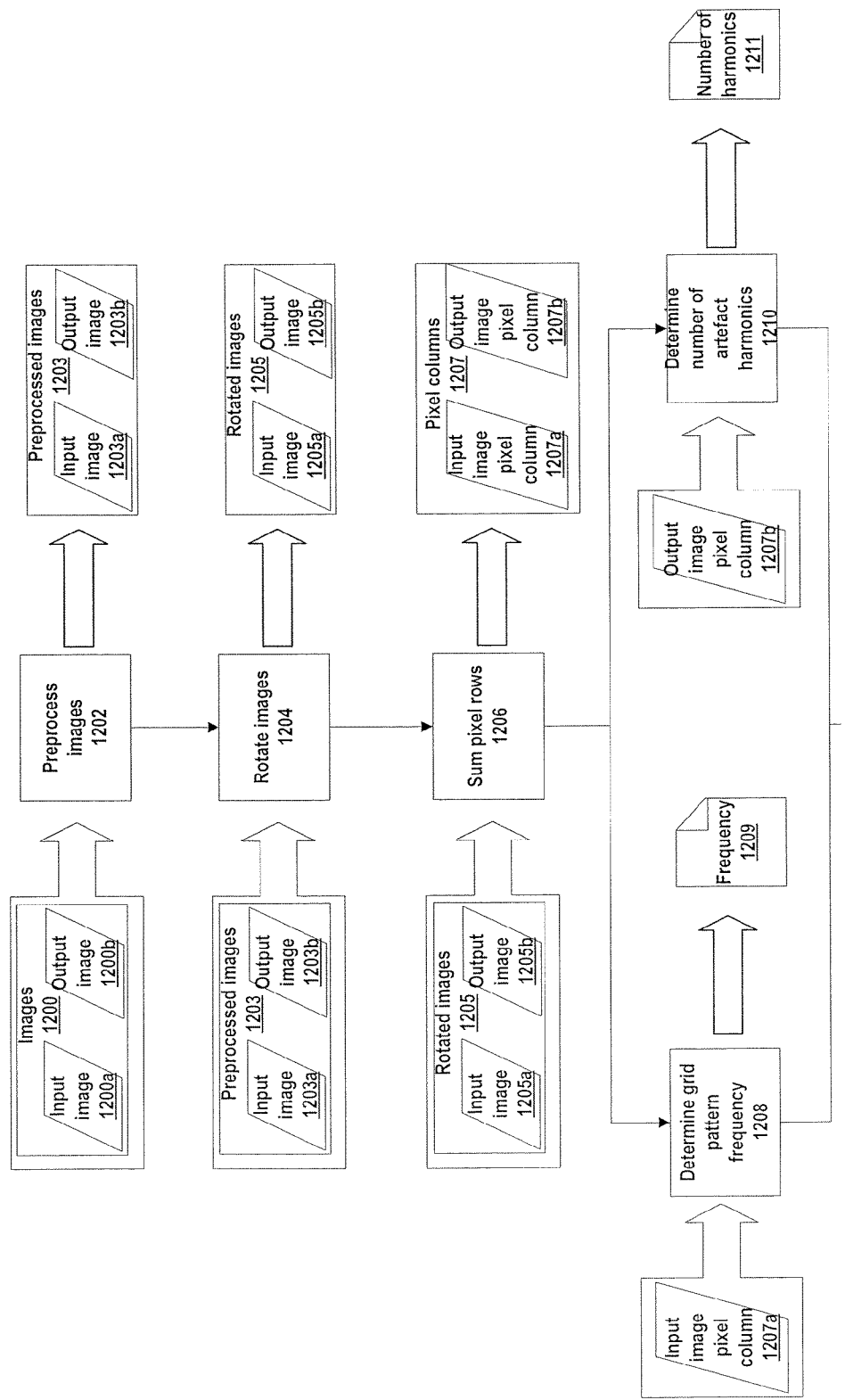
FIG. 12 is a flowchart that illustrates a procedure for removal of an artefact by subtraction of a sine wave representing the artefact, according to an example embodiment of the present invention.
Figure 12:
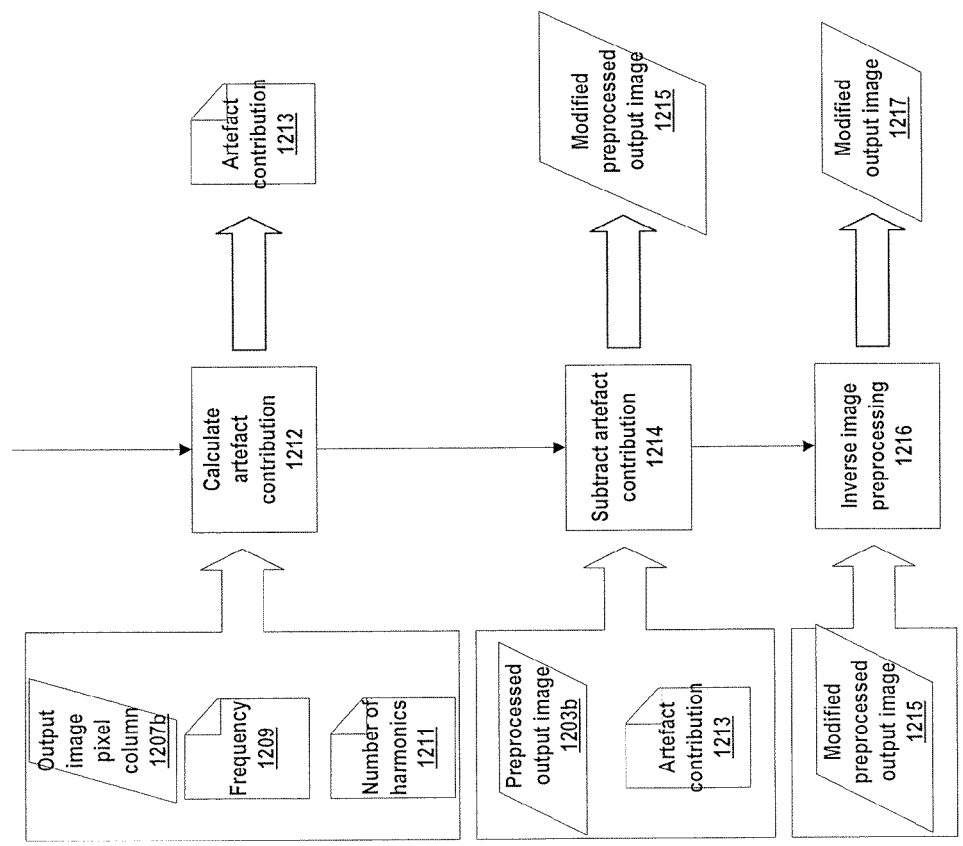

FIG. 12 is a flowchart that illustrates a procedure that may be performed, e.g., by the processor 108, for removal of an artefact from an output image, according to an example embodiment of the present invention. At 1202, images 1200 including an input image 1200a and an output image 1200b may be preprocessed to output preprocessed images 1203, including a preprocessed input image 1203a and a preprocessed output image 1203b that may have a more uniform sinusoidal variation in image intensities. At 1204, the preprocessed images 1203 may be rotated so that the projected grid line pattern of the input image 1203a and the artefact of the output image 1203b are parallel to the abscissas (assuming a vertical grid pattern of horizontal grid lines) of their respective imaging areas, if they were not previously parallel. At 1206, pixel values of some or all of the rows of the rotated images 1205 (assuming a vertical grid pattern of horizontal grid lines), including the rotated input image 1205a and the rotated output image 1205b, may be summed to produce pixel columns 1207, including an input image pixel column 1207a and an output image pixel column 1207b.

Subsequent to 1206, performance of 1208 and 1210 may be in sequence or concurrently, since performance of one is independent of the other. At 1208, the angular frequency 1209 of the grid pattern of the input image may be determined based on the input image pixel column 1207a. At 1210, the number of harmonics 1211 forming the artefact may be determined based on the output image pixel column 1207b.

At 1212, the artefact contribution 1213 to the preprocessed output image pixel values may be determined based on the output image pixel column 1207b (for the q matrix), the frequency 1209 (for the G matrix), and number of harmonics 1211 (for the G matrix). At 1214, the artefact contribution 1213 may be subtracted from the pixel values of the preprocessed output image 1203b to produce a modified preprocessed output image 1215. At 1216, an inverse of the image preprocessing may be performed on the modified preprocessed output image 1215 to produce a modified output image, which may be, practically speaking, the same as the output image 1200b excluding the artefact, if any.

In embodiments of the present invention according to which the artefact of an output image is removed by calculation of the artefact contribution and subtraction thereof from the pixel values of the output image, the artefact removal may be performed via 1208-1214, without performance of one or more, e.g., all, of 1202-1206, 1210, and 1216. For example, actual pixel values of the non-rotated output image 1200b, instead of preprocessed pixel values and/or row sums, may be used for the q matrix. Similarly, the angular frequency of the grid pattern of the input image 1200a may be determined based on the non-rotated, non-preprocessed, and non-row-summed original input image 1200a. Similarly, the non-preprocessed output image 1200b, the preprocessed output image 1203b, or a non-preprocessed output image pixel column may be used, instead of the output image pixel column 1207b, as input for determining the number of harmonics 1211. Further, instead of determining the number of harmonics 1211, a number, e.g., 3, may be assumed. Finally, if the output image 1200b is not preprocessed, taking an inverse of the preprocessing may be omitted. For example, 1214 would produce the modified output image 1217.

Additionally, in an example embodiment of the present invention, instead of determining the grid pattern frequency at 1208 for artefact removal, a grid pattern frequency determined prior to a procedure for artefact removal may be obtained at 1208.

In an alternative example embodiment of the present invention, for removal of an artefact from an optical sectioning output image, the system and method may remove a section of an image representing image transform data of the output image (referred to herein as a transform image) that is at a predetermined location of the transform image, i.e., a portion of the image transform data that forms the portion of the transform image that is at the predetermined location may be removed.

Figure 13:
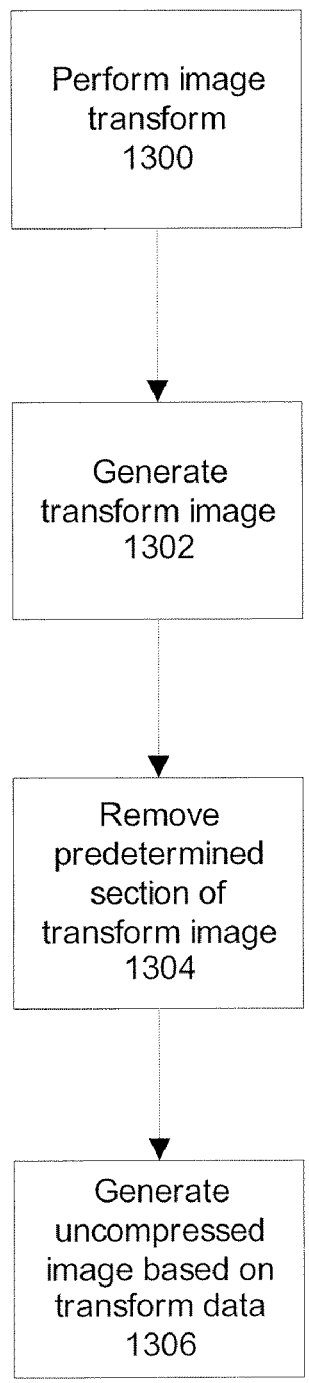
FIG. 13 is a flowchart that illustrates a procedure for removal of an artefact by modifying image compression data, according to an example embodiment of the present invention.

FIG. 13 is a flowchart that illustrates a procedure that may be performed, e.g., by the processor 108, for removal of an artefact from an output image via a corresponding transform image, according to an example embodiment of the present invention. At 1300, an image transform may be performed to produce image transform data. A non-exhaustive list of exemplary image transforms that may be used are a wavelet transform, a Discrete Cosine Transform (DCT), a Discrete Sine Transform (DST), a Fast Fourier Transform (FFT), a Hadamard Transform, a Hartley Transform, and a Discrete Wavelet Transform (DWT). Example DWT transforms may be a Haar Wavelet and a Daubechies Wavelet.

Figure 14:
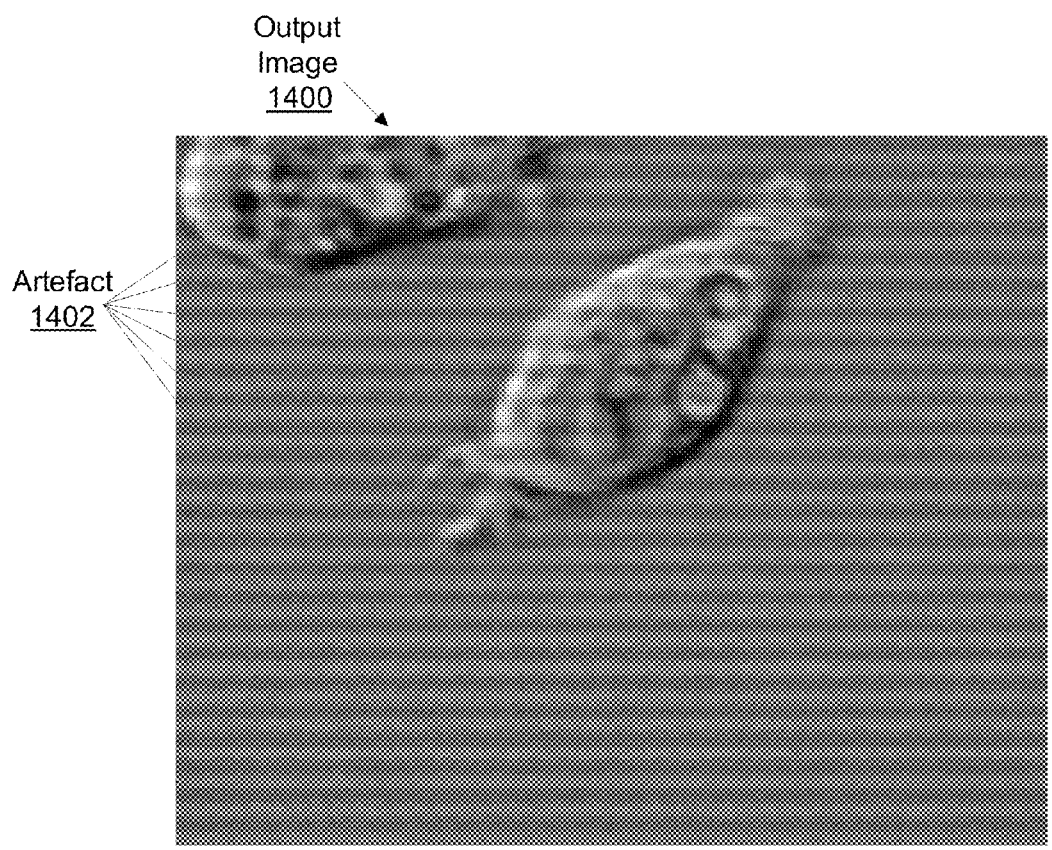
FIG. 14 is an example image including an artefact that may be generated via optical sectioning.
Figure 15:
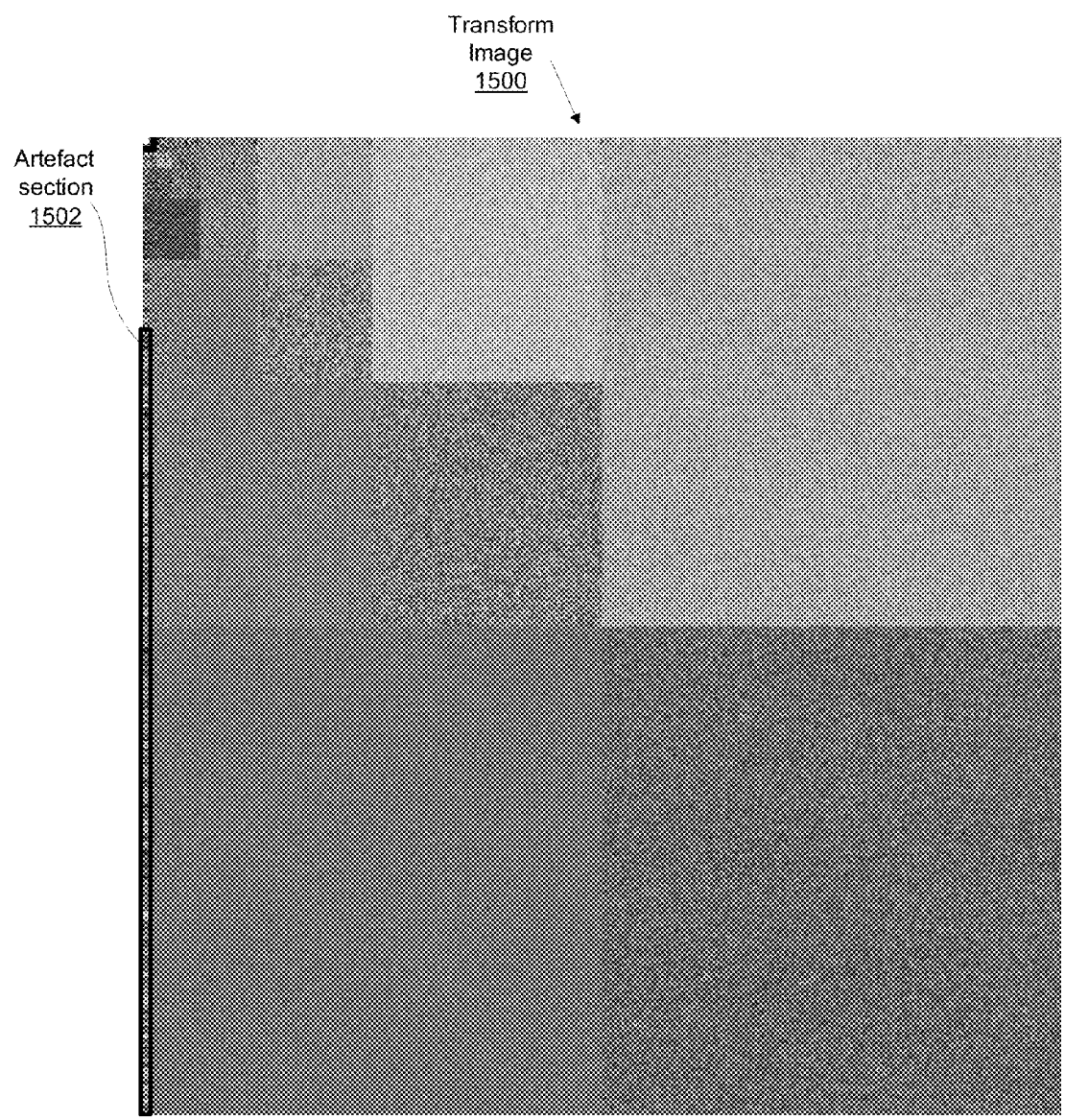
FIG. 15 is an example compression image that may be generated according to an example embodiment of the present invention.

At 1302, a transform image representing the image transform data may be generated. For example, FIG. 14 is an example output image 1400 including an artefact 1402 of a plurality of horizontal lines, some of which are singled out. FIG. 15 is an example transform image 1500 that may represent transform data generated by applying an image transform to the output image 1400.

At 1304, the system and method may remove a predetermined section of the generated transform image. The predetermined section may be a same defined area for any transform image representing transform data of an output image. The predetermined section may be that part of the transform image that corresponds to elements of the output image that are determined to be of low horizontal frequency and high vertical frequency (where the grid lines, and, therefore, the artefact are projected horizontally), in comparison to non-artefact elements of the output image. It may be assumed that the non-artefact elements would not be represented in that section of the transform image. In particular, where a transform image is such that the lower the row number of a pixel of the transform image, the lower the frequency in the vertical direction of the image element to which the pixel corresponds, and the lower the column number of the pixel of the transform image, the lower the frequency in the horizontal direction of the image element to which the pixel corresponds, the section may include approximately a bottom 80% of pixels of approximately 1 to 2% of consecutive pixel columns beginning at a left hand side of the transform image. However, other pixel and column percentages may be selected depending on the expected frequencies of the artefact. An example artefact section 1502 is traced in FIG. 15. Removal of the artefact section may set data corresponding to the artefact section to 0.

Figure 16:
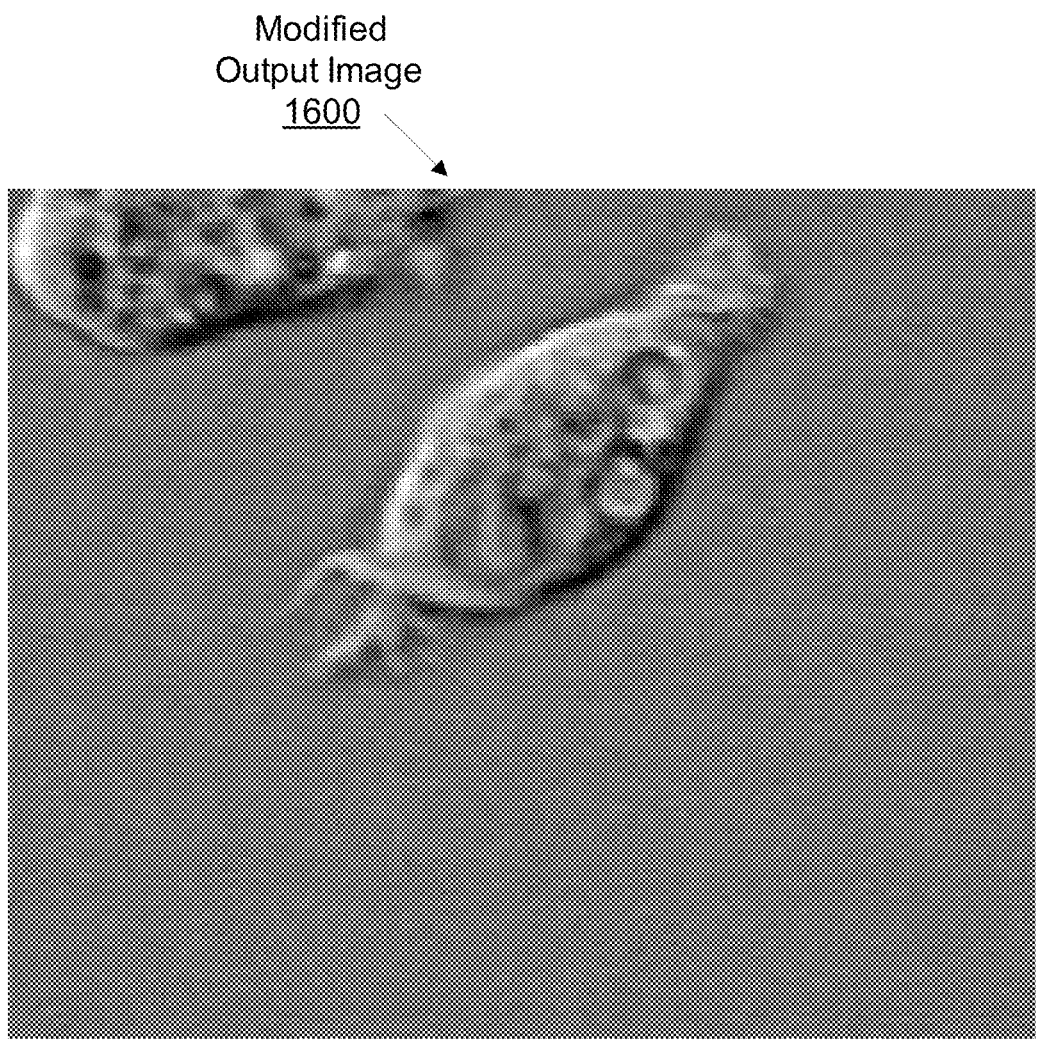
FIG. 16 is an example image that may be generated by removal of an artefact from an optical section image according to an example embodiment of the present invention.

At 1306, the system and method may perform an inverse transform to generate a non-transform image based on the modified transform data. The image generated at 1306 may be substantially the same as that of the output image, excluding the artefact. For example, FIG. 16 is an example modified output image 1600 generated by modified transform data corresponding to the output image 1400 of FIG. 14. The modified output image 1600 does not include the artefact 1402 shown in FIG. 14.

Those skilled in the art can appreciate from the foregoing description that the present invention can be implemented in a variety of forms. Therefore, while the embodiments of this invention have been described in connection with particular examples thereof, the true scope of the embodiments of the invention should not be so limited since other modifications will become apparent to the skilled practitioner upon a study of the drawings, specification, and following claims.

What is claimed is:

1. An image generation method, comprising:
    generating a first output image based on a plurality of input images;
    determining a contribution of an artefact to image intensity values of the first output image by determining values of coefficients of an equation representing a sinusoidal variation in one of a horizontal and a vertical direction;
    generating, by means of a processor, a second output image based on the first output image, the second output image being the same as the first output image less the artifact, including subtracting the contribution from the image intensity values, the subtraction including:
        determining values of the equation by plugging the determined coefficients into the equation; and
        subtracting the equation values from the image intensity values; and
    the equation values vary between one of pixel rows and pixel columns; wherein:
    the artefact is formed by a number of harmonics m of a grid pattern of at least one of the input images;
    the equation is $a_1 \cos(\omega y)+b_1 \sin(\omega y)+ \ldots a_m \cos(m\omega y)+ b_m \sin(m\omega y)$, wherein $a_1 \ldots a_m$ and $b_1 \ldots b_m$ are the coefficients, $\omega$ is an angular frequency of the grid pattern, and y is one of a pixel row number, which differs for each pixel row, and a pixel column number, which differs for each pixel column; and wherein
    the coefficients are determined by applying a regression analysis to matrices Q, b, and G;

$$Q = \begin{bmatrix} q_1 \\ q_2 \\ q_3 \\ \vdots \\ q_x \end{bmatrix},$$

wherein q is a sampled pixel intensity value of the first output image and x is a number of pixels sampled;

$$b = \begin{bmatrix} I \\ a_1 \\ b_1 \\ \vdots \\ a_m \\ b_m \end{bmatrix},$$

wherein I represents a sampled pixel intensity value less the artefact's contribution to the sampled pixel intensity; and $$G = \begin{bmatrix} 1 & \cos(\omega y_i) & \sin(\omega y_i) & \cos(2\omega y_i) & \sin(2\omega y_i) & \cos(3\omega y_i) & \sin(3\omega y_i) \\ 1 & \cos(\omega y_i) & \sin(\omega y_i) & \cos(2\omega y_i) & \sin(2\omega y_i) & \cos(3\omega y_i) & \sin(3\omega y_i) \\ 1 & \cos(\omega y_i) & \sin(\omega y_i) & \cos(2\omega y_i) & \sin(2\omega y_i) & \cos(3\omega y_i) & \sin(3\omega y_i) \\ \vdots & & & & & & \\ 1 & \cos(\omega y_i) & \sin(\omega y_i) & \cos(2\omega y_i) & \sin(2\omega y_i) & \cos(3\omega y_i) & \sin(3\omega y_i) \end{bmatrix},$$

wherein each row of the G matrix is associated with a corresponding value of the q matrix, and wherein, for each row of the G matrix, $y_i$ is one of a row number and a column number of the G matrix row's corresponding q matrix value.

2. The method of claim 1, wherein the coefficients are determined using least squares regression by applying a formula $b=(G^T G)^{-1} G^T$, wherein $G^T$ is a transpose of G.

3. The method of claim 1, further comprising:
    transforming image pixel values of the first output image to smoothen amplitudes of sinusoidal variations in image intensity across the first output image, the sinusoidal variations representing the artefact, wherein:
    the transformed values are sampled for the regression analysis;
    the contribution is subtracted from the transformed values; and
    generating the second output image further comprises performing an inverse of the image pixel values transformation subsequent to the subtracting the contribution from the image intensity values.

4. The method of claim 3, wherein the image pixel values of the first output image are transformed to their respective logarithmic values.

5. The method of claim 3, wherein:
the image pixel values of the first output image are transformed by applying an inverse hyperbolic sine function to $$\left(\frac{q'}{2}\right);$$

and q' represents an untransformed pixel value.

6. The method of claim 1, further comprising:
determining a tilt of the artefact in the first output image with respect to an imaging area of the first output image;
rotating the first output image to negate the tilt;
for each of a plurality of pixel rows of the first output image, summing pixel values of the row; and
inputting the row pixel value sums into the regression analysis.

7. The method of claim 1, further comprising:
determining the number of harmonics m.

8. The method of claim 1, wherein the number of harmonics m is preset to 3.

9. The method of claim 1, wherein the first output image is generated by optical sectioning.

10. An image generation method, comprising:
generating a first output image based on a plurality of input images;
determining a contribution of an artefact to image intensity values of the first output image by determining values of coefficients of an equation representing a sinusoidal variation in one of a horizontal and a vertical direction;
generating, by means of a processor, a second output image based on the first output image, the second output image being the same as the first output image less the artifact, including subtracting the contribution from the image intensity values, the subtraction including:
determining values of the equation by plugging the determined coefficients into the equation; and
subtracting the equation values from the image intensity values; and
the equation values vary between one of pixel rows and pixel columns; wherein:
the artefact is formed by a number of harmonics m of a grid pattern of at least one of the input images;
the equation is $a_1 \cos(\omega y) + b_1 \sin(\omega y) + \ldots a_m \cos(m\omega y) + b_m \sin(m\omega y)$, wherein $a_1 \ldots a_m$ and $b_1 \ldots b_m$ are the coefficients, $\omega$ is an angular frequency of the grid pattern, and y is one of a pixel row number, which differs for each pixel row, and a pixel column number, which differs for each pixel column; and wherein the angular frequency is determined via Bayesian Spectral Analysis.

11. The method of claim 10, wherein:
the angular frequency is determined by applying a formula $$p(\omega \mid d, I) \propto \frac{\left[d^T d - d^T G' (G'^T G')^{-1} G'^T d\right]^{\frac{M-N}{2}}}{\sqrt{\det(G'^T G')}};$$

$G'$ is a matrix $\begin{bmatrix} \cos\omega x_1 & \sin\omega x_1 & 1 \\ \cos\omega x_2 & \sin\omega x_2 & 1 \\ \cos\omega x_3 & \sin\omega x_3 & 1 \\ \vdots & \vdots & \\ \cos\omega x_N & \sin\omega x_N & 1 \end{bmatrix};$ x is an identification of a pixel location in one of the at least one input image and an image associated with the at least one input image from which corresponding data of the matrix is obtained;
M is a number of columns included in the G' matrix; and
N is a number of row included in the G' matrix.

12. The method of claim 10, further comprising:
transforming image pixel values of the at least one of the input images to smoothen amplitudes of sinusoidal variations in image intensity across the at least one of the input images, the sinusoidal variations representing the grid pattern, wherein the transformed values are input into the Bayesian Spectral Analysis.

13. The method of claim 12, wherein the image pixel values of the at least one of the input images are transformed to their respective logarithmic values.

14. The method of claim 12, wherein:
the image pixel values of the at least one of the input images are transformed by applying an inverse hyperbolic sine function to $$\left(\frac{q'}{2}\right);$$

and q' represents an untransformed pixel value.

15. The method of claim 10, further comprising:
determining a tilt of the grid pattern with respect to an imaging area of the at least one of the input images;
rotating the at least one of the input images to negate the tilt;
for each of a plurality of pixel rows of the at least one of the input images, summing pixel values of the row; and
inputting the row pixel value sums into the Bayesian Spectral Analysis.

16. An image generation method, comprising:
generating a first output image based on a plurality of input images;
determining a contribution of an artefact to image intensity values of the first output image by determining values of coefficients of an equation representing a sinusoidal variation in one of a horizontal and a vertical direction;
generating, by means of a processor, a second output image based on the first output image, the second output image being the same as the first output image less the artifact, including subtracting the contribution from the image intensity values, the subtraction including:
determining values of the equation by plugging the determined coefficients into the equation; and
subtracting the equation values from the image intensity values; and
the equation values vary between one of pixel rows and pixel columns; wherein:
the artefact is formed by a number of harmonics m of a grid pattern of at least one of the input images;

the equation is $a_1 \cos(\omega y)+b_1 \sin(\omega y)+ \ldots a_m \cos(m\omega y)+ b_m \sin(m\omega y)$, wherein $a_1 \ldots a_m$ and $b_1 \ldots b_m$ are the coefficients, $\omega$ is an angular frequency of the grid pattern, and y is one of a pixel row number, which differs for each pixel row, and a pixel column number, which differs for each pixel column; and wherein:

the grid pattern is included in each of the plurality of input images;

generating the first output image includes:
 recording the plurality of input images;
 calculating the angular frequency $\omega$;
 for at least one of the input images, calculating a phase angle of the input image's grid pattern based on the calculated angular frequency $\omega$; and
 for each pixel of the first output image, calculating a value in accordance with the calculated at least one phase angle and based on corresponding pixel values of the plurality of input images, the method further comprising:
  saving the calculated angular frequency $\omega$; and
  retrieving the saved angular frequency $\omega$ for determining the values of the equation.

17. An image generation method, comprising:

generating a first output image based on a plurality of input images;

determining a contribution of an artefact to image intensity values of the first output image by determining values of coefficients of an equation representing a sinusoidal variation in one of a horizontal and a vertical direction;

generating, by means of a processor, a second output image based on the first output image, the second output image being the same as the first output image less the artifact, including subtracting the contribution from the image intensity values, the subtraction including:
 determining values of the equation by plugging the determined coefficients into the equation; and
 subtracting the equation values from the image intensity values; and the equation values vary between one of pixel rows and pixel columns; wherein:

the artefact is formed by a number of harmonics m of a grid pattern of at least one of the input images;

the equation is $a_1 \cos(\omega y)+b_1 \sin(\omega y)+ \ldots a_m \cos(m\omega y)+ b_m \sin(m\omega y)$, wherein $a_1 \ldots a_m$ and $b_1 \ldots b_m$ are the coefficients, $\omega$ is an angular frequency of the grid pattern, and y is one of a pixel row number, which differs for each pixel row, and a pixel column number, which differs for each pixel column; and further comprising:

recording the plurality of input images;

calibrating an actuator that shifts a grid between each input image recordation, the grid pattern being formed by the grid; and calculating the angular frequency $\omega$ during the calibrating of the actuator.

18. An image generation method, comprising:

generating a first output image based on a plurality of input images; and generating, by means of a processor, a second output image based on the first output image, the second output image being the same as the first output image less an artifact, comprising:

applying an image transform to the first output image to obtain transform data;

deleting a predetermined portion of a transform image representing the transform data, the transform data being modified by the deleting of the predetermined portion; and generating a non-transform image based on the modified transform data; wherein the predetermined portion includes approximately a bottom 80% of approximately a left most 1% to 2% of consecutive pixel columns of the transform image.

19. The method of claim 18, wherein the image transform is one of a wavelet transform, a Discrete Cosine Transform (DCT), Discrete Sine Transform (DST), a Discrete Wavelet Transform (DWT), a Fast Fourier Transform (FFT), a Hadamard Transform, a Hartley Transform, a Haar Wavelet, and a Daubechies Wavelet.

20. A non-transitory computer-readable medium having stored thereon instructions adapted to be executed by a processor, the instructions which, when executed, cause the processor to perform an image generation method, the image generation method comprising:

generating a first output image based on a plurality of input images;

determining a contribution of an artefact to image intensity values of the first output image by determining values of coefficients of an equation representing a sinusoidal variation in one of a horizontal and a vertical direction;

generating a second output image based on the first output image, the second output image being the same as the first output image less the artefact, including subtracting the contribution from the image intensity values, the subtraction including:
 determining values of the equation by plugging the determined coefficients into the equation; and
 subtracting the equation values from the image intensity values; and the equation values vary between one of pixel rows and pixel columns; wherein:

the artefact is formed by a number of harmonics m of a grid pattern of at least one of the input images;

the equation is $a_1 \cos(\omega y)+b_1 \sin(\omega y)+ \ldots a_m \cos(m\omega y)+ b_m \sin(m\omega y)$, wherein $a_1 \ldots a_m$ and $b_1 \ldots b_m$ are the coefficients, $\omega$ is an angular frequency of the grid pattern, and y is one of a pixel row number, which differs for each pixel row, and a pixel column number, which differs for each pixel column; and wherein the coefficients are determined by applying a regression analysis to matrices Q, b, and G;

$$Q = \begin{bmatrix} q_1 \\ q_2 \\ q_3 \\ \vdots \\ q_x \end{bmatrix},$$

wherein q is a sampled pixel intensity value of the first output image and x is a number of pixels sampled;

$$b = \begin{bmatrix} I \\ a_1 \\ b_1 \\ \vdots \\ a_m \\ b_m \end{bmatrix},$$

wherein I represents a sampled pixel intensity value less the artefact's contribution to the sampled pixel intensity; and $$G = \begin{bmatrix} 1 & \cos(\omega y_i) & \sin(\omega y_i) & \cos(2\omega y_i) & \sin(2\omega y_i) & \cos(3\omega y_i) & \sin(3\omega y_i) \\ 1 & \cos(\omega y_i) & \sin(\omega y_i) & \cos(2\omega y_i) & \sin(2\omega y_i) & \cos(3\omega y_i) & \sin(3\omega y_i) \\ 1 & \cos(\omega y_i) & \sin(\omega y_i) & \cos(2\omega y_i) & \sin(2\omega y_i) & \cos(3\omega y_i) & \sin(3\omega y_i) \\ \vdots \\ 1 & \cos(\omega y_i) & \sin(\omega y_i) & \cos(2\omega y_i) & \sin(2\omega y_i) & \cos(3\omega y_i) & \sin(3\omega y_i) \end{bmatrix},$$

wherein each row of the G matrix is associated with a corresponding value of the q matrix, and wherein, for each row of the G matrix, $y_i$ is one of a row number and a column number of the G matrix row's corresponding q matrix value.

21. An imaging apparatus, comprising:
a camera for recording a plurality of input images; and
a processor configured to:
generate a first output image based on the plurality of input images;
determine a contribution of an artefact to image intensity values of the first output image by determining values of coefficients of an equation representing a sinusoidal variation in one of a horizontal and a vertical direction;
remove an artefact from the first output image to generate a second output image by:
subtracting the contribution from the image intensity values, the subtraction including:
determining values of the equation by plugging the determined coefficients into the equation; and
subtracting the equation values from the image intensity values; and the equation values vary between one of pixel rows and pixel columns;
wherein:
the artefact is formed by a number of harmonics m of a grid pattern of at least one of the input images;
the equation is $a_1 \cos(\omega y) + b_1 \sin(\omega y) + \ldots a_m \cos(m\omega y) + b_m \sin(m\omega v)$, wherein $a_1 \ldots a_m$ and $b_1 \ldots b_m$ are the coefficients, $\omega$ is an angular frequency of the grid pattern, and y is one of a pixel row number, which differs for each pixel row, and a pixel column number, which differs for each pixel column; and wherein
the coefficients are determined by applying a regression analysis to matrices Q, b, and G;

$$Q = \begin{bmatrix} q_1 \\ q_2 \\ q_3 \\ \vdots \\ q_x \end{bmatrix},$$

wherein q is a sampled pixel intensity value of the first output image and x is a number of pixels sampled;

$$b = \begin{bmatrix} I \\ a_1 \\ b_1 \\ \vdots \\ a_m \\ b_m \end{bmatrix},$$

wherein I represents a sampled pixel intensity value less the artefact's contribution to the sampled pixel intensity; and $$G = \begin{bmatrix} 1 & \cos(\omega y_i) & \sin(\omega y_i) & \cos(2\omega y_i) & \sin(2\omega y_i) & \cos(3\omega y_i) & \sin(3\omega y_i) \\ 1 & \cos(\omega y_i) & \sin(\omega y_i) & \cos(2\omega y_i) & \sin(2\omega y_i) & \cos(3\omega y_i) & \sin(3\omega y_i) \\ 1 & \cos(\omega y_i) & \sin(\omega y_i) & \cos(2\omega y_i) & \sin(2\omega y_i) & \cos(3\omega y_i) & \sin(3\omega y_i) \\ \vdots \\ 1 & \cos(\omega y_i) & \sin(\omega y_i) & \cos(2\omega y_i) & \sin(2\omega y_i) & \cos(3\omega y_i) & \sin(3\omega y_i) \end{bmatrix},$$

wherein each row of the G matrix is associated with a corresponding value of the q matrix, and wherein, for each row of the G matrix, $y_i$ is one of a row number and a column number of the G matrix row's corresponding q matrix value.

22. The imaging apparatus of claim 21, wherein the coefficients are determined via a least squares regression by an application of a formula $b=(G^T G)^{-1} G^T$, wherein $G^T$ is a transpose of G.

23. The imaging apparatus of claim 21, wherein:
the processor is configured to transform image pixel values of the first output image to smoothen amplitudes of sinusoidal variations in image intensity across the first output image, the sinusoidal variations representing the artefact;
the transformed values are sampled for the regression analysis;
the contribution is subtracted from the transformed values; and
the generation of the second output image includes performance of an inverse of the image pixel values transformation subsequent to the subtraction of the contribution from the image intensity values.

24. The imaging apparatus of claim 23, wherein the image pixel values of the first output image are transformed to their respective logarithmic values.

25. The imaging apparatus of claim 23, wherein:
the image pixel values of the first output image are transformed by applying an inverse hyperbolic sine function to $$\left(\frac{q'}{2}\right);$$

and
q' represents an untransformed pixel value.

26. The imaging apparatus of claim 21, wherein the processor is configured to:
determine a tilt of the artefact in the first output image with respect to an imaging area of the first output image;
rotate the first output image to negate the tilt;

for each of a plurality of pixel rows of the first output image, sum pixel values of the row; and input the row pixel value sums into the regression analysis.

27. The imaging apparatus of claim 21, wherein the processor is configured to:

determine the number of harmonics m.

28. The imaging apparatus of claim 21, wherein the number of harmonics m is preset to 3.

29. The imaging apparatus of claim 21, wherein the first output image is generated by optical sectioning.

30. An imaging apparatus, comprising:

a camera for recording a plurality of input images; and a processor configured to:

generate a first output image based on the plurality of input images;

determine a contribution of an artefact to image intensity values of the first output image by determining values of coefficients of an equation representing a sinusoidal variation in one of a horizontal and a vertical direction;

remove an artefact from the first output image to generate a second output image by:

subtracting the contribution from the image intensity values, the subtraction including:

determining values of the equation by plugging the determined coefficients into the equation; and subtracting the equation values from the image intensity values; and the equation values vary between one of pixel rows and pixel columns;

wherein:

the artefact is formed by a number of harmonics m of a grid pattern of at least one of the input images;

the equation is $a_1 \cos(\omega y)+b_1 \sin(\omega y)+ \ldots a_m \cos(m\omega y)+ b_m \sin(m\omega y)$, wherein $a_1 \ldots a_m$ and $b_1 \ldots b_m$ are the coefficients, $\omega$ is an angular frequency of the grid pattern, and y is one of a pixel row number, which differs for each pixel row, and a pixel column number, which differs for each pixel column; and wherein the angular frequency is determined via Bayesian Spectral Analysis.

31. The imaging apparatus of claim 30, wherein:

the angular frequency is determined by an application of a formula $$p(\omega \mid d, I) \propto \frac{[d^T d - d^T G'(G'^T G')^{-1} G'^T d]^{\frac{M-N}{2}}}{\sqrt{\det(G'^T G')}};$$

$$G' \text{ is a matrix} \begin{bmatrix} \cos\omega x_1 & \sin\omega x_1 & 1 \\ \cos\omega x_2 & \sin\omega x_2 & 1 \\ \cos\omega x_3 & \sin\omega x_3 & 1 \\ \vdots & \vdots & \vdots \\ \cos\omega x_N & \sin\omega x_N & 1 \end{bmatrix};$$

x is an identification of a pixel location in one of the at least one input image and an image associated with the at least one input image from which corresponding data of the matrix is obtained;

M is a number of columns included in the G' matrix; and

N is a number of row included in the G' matrix.

32. The imaging apparatus of claim 30, wherein:

the processor is configured to transform image pixel values of the at least one of the input images to smoothen amplitudes of sinusoidal variations in image intensity across the at least one of the input images;

the sinusoidal variations represent the grid pattern; and the transformed values are input into the Bayesian Spectral Analysis.

33. The imaging apparatus of claim 32, wherein the image pixel values of the at least one of the input images are transformed to their respective logarithmic values.

34. The imaging apparatus of claim 32, wherein:

the image pixel values of the at least one of the input images are transformed by applying an inverse hyperbolic sine function to $$\left(\frac{q'}{2}\right);$$

and q' represents an untransformed pixel value.

35. The imaging apparatus of claim 30, wherein the processor is configured to:

determine a tilt of the grid pattern with respect to an imaging area of the at least one of the input images;

rotate the at least one of the input images to negate the tilt;

for each of a plurality of pixel rows of the at least one of the input images, sum pixel values of the row; and input the row pixel value sums into the Bayesian Spectral Analysis.

36. An imaging apparatus, comprising:

a camera for recording a plurality of input images; and a processor configured to:

generate a first output image based on the plurality of input images;

determine a contribution of an artefact to image intensity values of the first output image by determining values of coefficients of an equation representing a sinusoidal variation in one of a horizontal and a vertical direction;

remove an artefact from the first output image to generate a second output image by:

subtracting the contribution from the image intensity values, the subtraction including:

determining values of the equation by plugging the determined coefficients into the equation; and subtracting the equation values from the image intensity values; and the equation values vary between one of pixel rows and pixel columns;

wherein:

the artefact is formed by a number of harmonics m of a grid pattern of at least one of the input images;

the equation is $a_1 \cos(\omega y)+b_1 \sin(\omega y)+ \ldots a_m \cos(m\omega y)+ b_m \sin(m\omega y)$, wherein $a_1 \ldots a_m$ and $b_1 \ldots b_m$ are the coefficients, $\omega$ is an angular frequency of the grid pattern, and y is one of a pixel row number, which differs for each pixel row, and a pixel column number, which differs for each pixel column; and wherein:

the grid pattern is included in each of the plurality of input images;

the generation of the first output image includes:

a recordation of the plurality of input images;

a calculation of the angular frequency $\omega$;

for at least one of the input images, a calculation of a phase angle of the input image's grid pattern based on the calculated angular frequency $\omega$; and for each pixel of the first output image, a calculation of a value in accordance with the calculated at least one phase angle and based on corresponding pixel values of the plurality of input images; and the processor is configured to:
save the calculated angular frequency ω; and
retrieve the saved angular frequency ω for determination of the values of the equation.

37. An imaging apparatus, comprising:
a camera for recording a plurality of input images; and
a processor configured to:
generate a first output image based on the plurality of input images;
determine a contribution of an artefact to image intensity values of the first output image by determining values of coefficients of an equation representing a sinusoidal variation in one of a horizontal and a vertical direction;
remove an artefact from the first output image to generate a second output image by:
subtracting the contribution from the image intensity values, the subtraction including:
determining values of the equation by plugging the determined coefficients into the equation; and
subtracting the equation values from the image intensity values; and the equation values vary between one of pixel rows and pixel columns;
wherein:
the artefact is formed by a number of harmonics m of a grid pattern of at least one of the input images;
the equation is $a_1 \cos(\omega y) + b_1 \sin(\omega y) + \ldots a_m \cos(m\omega y) + b_m \sin(m\omega y)$, wherein $a_1 \ldots a_m$ and $b_1 \ldots b_m$ are the coefficients, ω is an angular frequency of the grid pattern, and y is one of a pixel row number, which differs for each pixel row, and a pixel column number, which differs for each pixel column; and further comprising:
a lamp;
a grid, the grid pattern being formed by shining light of the lamp at the grid; and
an actuator for shifting the grid between each input image recordation, wherein the processor is configured to:
calibrate the actuator; and
calculate the angular frequency ω during the calibration of the actuator.

38. An imaging apparatus, comprising:
a camera for recording a plurality of input images; and
a processor configured to:
generate a first output image based on the plurality of input images; and
remove an artefact from the first output image to generate a second output image;
wherein, for the generation of the second output image, the processor is configured to:
apply an image transform to the first output image to obtain transform data;
delete a predetermined portion of a transform image representing the transform data, the transform data being modified by the deletion of the predetermined portion; and
generate a non-transform image based on the modified transform data, and
wherein the predetermined portion includes approximately a bottom 80% of approximately a left most 1% to 2% of consecutive pixel columns of the transform image.

39. The imaging apparatus of claim 38, wherein the image transform is one of a wavelet transform, a Discrete Cosine Transform (DCT), Discrete Sine Transform (DST), a Discrete Wavelet Transform (DWT), a Fast Fourier Transform (FFT), a Hadamard Transform, a Hartley Transform, a Haar Wavelet, and a Daubechies Wavelet.

40. A system for optical section imaging, comprising:
a camera for recording a plurality of input images of an imaging surface;
a grid;
a lamp for shining light at the grid to project a grid pattern onto the imaging surface so that each of the input images includes a corresponding grid pattern at a corresponding phase angle;
an actuator for shifting the grid between each input image recordation so that the grid patterns of at least two of the plurality of input images are at different phase angles; and
a processor configured to:
calculate, for each of the plurality of input images, the image's grid pattern phase angle;
generate a first output image by calculating for each pixel of the first output image a value in accordance with a corresponding pixel value of each of the plurality of input images and the calculated phase angles; and
generate a second output image by removing an artefact included in the first output image, wherein the artefact is removed one of:
by (a):
determining a contribution of the artefact to image intensity values of the first output image; and
subtracting the contribution from the image intensity values; and
by (b):
applying an image transform to the first output image to obtain transform data;
deleting a predetermined portion of a transform image representing the transform data, the transform data being modified by the deletion of the predetermined portion; and
generating a non-transform image based on the modified transform data.

* * * * *